United States Patent
Yamashita et al.

(10) Patent No.: US 6,750,192 B2
(45) Date of Patent: Jun. 15, 2004

(54) SURFACTANT, PROCESS FOR PRODUCING THE SAME AND DETERGENT COMPOSITION

(75) Inventors: Seiji Yamashita, Kyoto (JP); Masahiro Matsuoka, Kyoto (JP); Kunio Nagai, Kyoto (JP); Atsushi Oota, Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 300 days.

(21) Appl. No.: 09/819,769

(22) Filed: Mar. 29, 2001

(65) Prior Publication Data

US 2002/0019327 A1 Feb. 14, 2002

Related U.S. Application Data

(63) Continuation of application No. PCT/JP99/05305, filed on Sep. 29, 1999.

(30) Foreign Application Priority Data

| Sep. 29, 1998 | (JP) | 10-274563 |
| Apr. 27, 1999 | (JP) | 11-120300 |
| May 26, 1999 | (JP) | 11-146489 |
| Sep. 8, 1999 | (JP) | 11-254772 |

(51) Int. Cl.$^7$ .............. C11D 1/72; C11D 3/20; C11D 3/43
(52) U.S. Cl. ............ 510/421; 510/119; 510/130; 510/137; 510/138; 510/235; 510/506
(58) Field of Search .............. 510/119, 130, 510/137, 138, 235, 421, 506

(56) References Cited

U.S. PATENT DOCUMENTS

| 4,396,779 A | * | 8/1983 | Edwards | 568/618 |
| 4,453,023 A | * | 6/1984 | McCain et al. | 568/618 |
| 5,981,456 A | * | 11/1999 | Tartakovsky et al. | 510/220 |
| 5,981,457 A | * | 11/1999 | Ahmed | 510/223 |

FOREIGN PATENT DOCUMENTS

| EP | 043963 | * | 1/1982 |
| EP | 092256 | * | 10/1983 |
| EP | 180266 | * | 5/1986 |
| EP | 180267 | * | 5/1986 |
| EP | 228121 | * | 7/1987 |
| EP | 361616 | * | 4/1990 |
| EP | 361619 | * | 4/1990 |
| GB | 2080303 | * | 2/1982 |

* cited by examiner

Primary Examiner—Gregory Delcotto
(74) Attorney, Agent, or Firm—Connolly Bove Lodge & Hutz LLP

(57) ABSTRACT

A nonionic surfactant comprising an aliphatic alcohol alkylene oxide adduct (A), directly produced by adding an alkylene oxide (b1) to an aliphatic alcohol (a1),
and satisfying the following (i), (ii) and (iii):
(i) comprising one compound, or a mixture of two or more $$R^1O\text{—}[(C_2H_4O)_m/(AO)_n]\text{—}(C_2H_4O)_p\text{—}H \qquad (1)$$

(ii) having a ratio Mw/Mn within the specific range; and
(iii) having a distribution constant (c), determined by the following equation (4), of 1.0 or less:

$$c=(v+n_0/n_{00}-1)/[\mathrm{Ln}(n_{00}/n_0)++n_0/n_{00}-1] \qquad (4).$$

This invention provides an aliphatic alcohol alkylene oxide adduct, having surface activities comparable to alkylphenol-based nonionic surfactants and moreover having no fear of environmental endocrine disrupters like alkylphenol-based nonionic surfactants.

This invention provides a detergent composition using the above anionic surfactant and having excellent detergency.

14 Claims, No Drawings

SURFACTANT, PROCESS FOR PRODUCING THE SAME AND DETERGENT COMPOSITION

CROSS-REFERENCE TO RELATED APPLICATION

This is a continuation of international application PCT/JP99/05305, filed Sep. 29, 1999, which designated the U.S.

FIELD OF THE INVENTION

The present invention relates to a novel nonionic surfactant, an anionic surfactant anionizing it and a detergent composition. More specifically, the invention relates to non-alkylphenol type nonionic and anionic surfactants.

BACKGROUND ART

Heretofore, aliphatic alcohol alkylene oxide adducts, obtained by addition-polymerizing an alkylene oxide with aliphatic alcohols in the presence of a basic catalyst or an acidic catalyst, and anionized products thereof have been known as various surfactants, solvents, intermediates for chemicals. As compared with alkylphenol-based nonionic surfactants, aliphatic alcohol alkylene oxide adducts known heretofore, however, do not manifest sufficient surface activity in some case, for instance, result in insufficient emulsifiability, emulsion stability and low-foaming properties when used as emulsifiers. With respect to anionized products of aliphatic alcohol alkylene oxide adducts, there have been remained problems of foaming properties, detergency, stability with time of products and irritation to human skin.

In addition, there has been known a method using perchlorates as catalysts for addition of an alkylene oxide (U.S. Pat. No. 4,112,231). This method has not yet become industrially used; since the catalysts are of low catalytic activity, and, when used in an increased amount to shorten the reaction time, they cause problems such that the resulting product severely discolored to result in worsened product appearance and that the product contains aldehyde in high content.

The inventors have devoted deep study to resolve the above problems, and have found that nonionic surfactants comprising aliphatic alcohol alkylene oxide adducts having a specific composition and a specific molecular weight distribution exhibit excellent emulsifiability and detergency. Besides, they have found that such aliphatic alcohol alkylene oxide adducts can be directly produced by using two specific catalysts in combination to reach the present invention. Further, it has been found that products obtained by anionizing the resulting aliphatic alcohol alkylene oxide adducts have improved foaming properties, detergency, stability with time of products and irritation to human skin.

It is an object of the present invention to provide an aliphatic alcohol alkylene oxide adduct, having surface activities comparable to alkylphenol-based nonionic surfactants and moreover having no fear of environmental endocrine disrupters like alkylphenol-based nonionic surfactants.

It is another object of this invention to provide an anionic surfactant having improved foaming properties, detergency, stability with time of products and irritation to human skin by anionizing an aliphatic alcohol alkylene oxide adduct.

It is still another object of this invention to provide a detergent composition using the above anionic surfactant and having excellent detergency.

SUMMARY OF THE INVENTION

Thus, according to the present invention, provided are the following (I), (II), (III) and (IV).

(I) A nonionic surfactant comprising an aliphatic alcohol alkylene oxide adduct (A), said (A) being directly produced by adding an alkylene oxide (b1) to an aliphatic alcohol (a1) and satisfying the following (i), (ii) and (iii):

(i) It comprises one compound represented by the following general formula (1) or a mixture of two or more thereof.

$$R^1O\text{—}[(C_2H_4O)_m/(AO)_n]\text{—}(C_2H_4O)_p\text{—}H \tag{1}$$

In the formula, $R^1$ is an aliphatic hydrocarbon group containing 8–24 carbon atoms or a cycloaliphatic hydrocarbon group containing 8–24 carbon atoms; A is an alkylene group containing at least 3 carbon atoms; m is 0 or an integer of 1 or more, the average thereof being in the range of 0–4, n is 0 or an integer of 1 or more, the average thereof being in the range of 0–3, p is 0 or an integer of 1 or more, the average thereof being in the range of 1–80, (m+n+p) is an integer, the average thereof being in the range of 3–81, and average of (m+p)/(m+n+p) is at least 0.5. In case of m≠0 and n≠0, $[(C_2H_4O)_m/(AO)_n]$ represents block addition or random addition.

(ii) The ratio Mw/Mn of a weight-average molecular weight (Mw) to a number-average molecular weight (Mn) satisfies the following relation (2) or (3).

$$Mw/Mn \leq 0.030 \times Ln(v) + 1.010 \text{ (in case of } v<10) \tag{2}$$

$$Mw/Mn \leq -0.026 \times Ln(v) + 1.139 \text{ (in case of } v \geq 10) \tag{3}$$

Herein, v represents the average of (m+n+p) in the above general formula (1).

(iii) A distribution constant (c), determined by the following equation (4) derived from Weibull distribution law, is 1.0 or less. This is required only in the case of v up to 12.

$$c=(v+n_0/n_{00}-1)/[Ln(n_{00}/n_0)+n_0/n_{00}-1] \tag{4}$$

Herein, v is the same in the above, $n_{00}$, is the molar number of the aliphatic alcohol (a1) used in the reaction, and $n_0$ is the molar number of the aliphatic alcohol (a1) unreacted.

(II) A process for producing an aliphatic alcohol alkylene oxide adduct, which comprises addition reaction of an aliphatic alcohol alkylene oxide adduct (e), obtainable by adding 1–2.5 moles on the average of an alkylene oxide (b2) containing at least two carbon atoms to an aliphatic alcohol (a2) containing 1–24 carbon atoms in the presence of a catalyst (d) providing an adduct having a distribution constant c' of 1.0 or less as determined by the following equation (4') derived from Weibull distribution law, with an alkylene oxide (b3) containing at least two carbon atoms in the presence of an alkaline catalyst (f).

$$c'=(v'+n_0'/n_{00}'-1)/[Ln(n_{00}'/n_0')+n_0'/n_{00}'-1] \tag{4'}$$

Herein, v' represents the average addition molar number of alkylene oxide added per 1 mole of the aliphatic alcohol (a2), $n_{00}'$ represents the molar number of the aliphatic alcohol (a2) used in the reaction, and $n_0'$ represents the molar number of the aliphatic alcohol (a2) unreacted.

(III) An anionic surfactant obtainable by anionization of an aliphatic alcohol alkylene oxide adduct (A'), said (A') being directly produced by adding an alkylene oxide (b1) to an aliphatic alcohol (a1) and satisfying the following (ii'), (iii') and (iv).

(ii') The ratio Mw/Mn of a weight-average molecular weight (Mw) to a number-average molecular weight (Mn) satisfies the following relation (2') or (3').

$$Mw/Mn \leq 0.030 \times Ln(v'') + 1.010 \text{ (in case of } v''<10) \quad (2')$$

$$Mw/Mn \leq -0.026 \times Ln(v'') + 1.139 \text{ (in the case of } v'' \geq 10) \quad (3')$$

Herein, v" represents the average of (m'+n'+p') in the following general formula (1').
(iii') A distribution constant c", determined by the following equation (4"), is 1.0 or less. This is required only in the case of v" up to 12.

$$c'' = (v'' + n_0/n_{00} - 1)/[Ln(n_{00}/n_0) + n_0/n_{00} - 1] \quad (4'')$$

Herein, v" is the same in the above. $n_{00}$ represents the molar number of the aliphatic alcohol (a1) used in the reaction, and $n_0$ represents the molar number of the aliphatic alcohol (a1) unreacted.
(iv) It comprises one compound represented by the following general formula (1') or a mixture of two or more thereof.

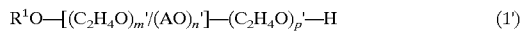
$$R^1O—[(C_2H_4O)_{m'}/(AO)_{n'}]—(C_2H_4O)_{p'}—H \quad (1')$$

Herein, $R^1$ is an aliphatic hydrocarbon group containing 8–24 carbon atoms or a cycloaliphatic hydrocarbon group containing 8–24 carbon atoms; A is an alkylene group containing at least 3 carbon atoms; m' is 0 or an integer of 1 or more, the average thereof being in the range of 0–5, n' is 0 or an integer of 1 or more, the average thereof being in the range of 0–5, p' is 0 or an integer of 1 or more, the average thereof being in the range of 0–10, (m'+n'+p') is an integer, the average thereof being in the range of 1–20, and average of (m'+p')/(m'+n'+p') is at least 0.5. In case of m'≠0 and n'≠0 [$(C_2H_4O)_{m'}/(AO)_{n'}$] represents block addition or random addition.
(IV) A detergent composition comprising the above anionic surfactant.

DETAILED DISCLOSURE OF THE INVENTION
(I) Nonionic Surfactant

In the invention of the above (I), said aliphatic alcohol alkylene oxide adduct (A) is one or a mixture of two or more of an aliphatic alcohol alkylene oxide adduct directly produced by adding an alkylene oxide (b1) to an aliphatic alcohol (a1) (In this specification, "aliphatic alcohol" is defined as including both aliphatic alcohol and cycloaliphatic alcohol.)

The term "directly produced" used herein means that said adducts are directly produced without any operation for fractionating unreacted alcohol or adducts of different addition molar numbers, such as through fractional distillation. Ones requiring fractionation are of no practical use to be used as usual nonionic surfactants, because of complicated process. But, ones obtained by stripping low-boiling matters or unreacted alcohol with easy operation not for the purpose of fractionation are not included.

The above (A) comprises one represented by the following general formula (1) or a mixture of two or more thereof.

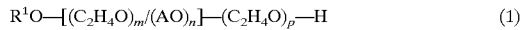
$$R^1O—[(C_2H_4O)_m/(AO)_n]—(C_2H_4O)_p—H \quad (1)$$

In the above formula (1), $R^1$ is a residue of an aliphatic alcohol (a1), and represents an aliphatic hydrocarbon group or a cycloaliphatic hydrocarbon group, containing usually 8–24 (preferably 12–18) carbon atoms. Desirable emulsifiability, solubilizing power and detergency are not attained if carbon atoms in $R^1$ are less then 8; while carbon atoms in $R^1$ exceeding 24 is not preferred with respect to handling because of increased pouring point of the resulting alkylene oxide adduct. The above aliphatic hydrocarbon groups include straight-chain or branched, saturated or unsaturated aliphatic hydrocarbon groups (alkyl, alkenyl and alkadienyl groups); and the above cycloaliphatic hydrocarbon groups include cycloalkyl groups and polycyclic hydrocarbon groups.

Concrete examples of $R^1$ include alkyl groups, such as octyl, nonyl, decyl, dodecyl, tridecyl, tetradecyl, hexa-decyl, octadecyl, nonadecyl, 2-ethylhexyl and 2-ethyloctyl groups. Illustrative of alkenyl groups are octenyl, decenyl, dodecenyl, tridecenyl, pentadecenyl, oleyl and gadoleyl groups. Alkadienyl groups are inclusive of linoleyl group. Exemplary of cycloalkyl groups are ethylcyclohexyl, propylcyclohexyl, octylcyclohexyl and nonylcyclohexyl groups. Polycyclic hydrocarbon groups include, for example, adamantyl group.

Aliphatic alcohols (a1) used in this invention, providing the residue $R^1$, are alcohols containing usually 8–24 (preferably 12–18) carbon atoms and may be natural alcohols or synthetic alcohols (such as Ziegler alcohols and oxo alcohols).

Illustrative examples include saturated aliphatic alcohols, such as octyl alcohol, nonyl alcohol, decyl alcohol, undecyl alcohol, dodecyl alcohol, tridecyl alcohol, tetradecyl alcohol, hexadecyl alcohol, octadecyl alcohol and nonadecyl alcohol; unsaturated aliphatic alcohols, such as octenyl alcohol, decenyl alcohol, dodecenyl alcohol, tridecenyl alcohol, pentadecenyl alcohol, oleyl alcohol, gadoleyl alcohol and linoleyl alcohol; cycloaliphatic alcohols, such as ethylcyclohexyl alcohol, propylcyclohexyl alcohol, octylcyclohexyl alcohol, nonylcyclohexyl alcohol and adamantyl alcohol. There may be used one or two or more of these. Among these aliphatic alcohols, preferred are primary or secondary ones and more preferred are primary ones. Besides, the alkyl group moiety may be linear or branched. Particularly preferred are dodecyl alcohol, tridecyl alcohol, tetradecyl alcohol, hexadecyl alcohol and octadecyl alcohol.

In the above formula (1), the part of $(C_2H_4O)$ is formed by addition of ethylene oxide (hereinafter referred to as EO). A represents an alkylene group containing at least 3 carbon atoms, preferably 3–8 carbon atoms, particularly preferably 3 carbon atoms. The part of (AO) is formed by addition of an alkylene oxide containing at least 3 carbon atoms. As such an alkylene oxide, there may be mentioned propylene oxide (hereinafter referred to as PO), 1,2- or 2,3-butylene oxide, tetrahydrofran, styrene oxide and the like. Preferred is PO.

In the above general formula (1), m is 0 or an integer of 1 or more, giving an average of usually 0–4, preferably 0–3, particularly 1–3. In general, n is 0 or an integer of 1 or more, giving an average of usually 0–3, and is preferably 0, 1 or 2. Usually, p is 0 or an integer of 1 or more, giving an average of 1–80, preferably 2–70, more preferably 3–40, most preferably 3–20. When it exceeds 80, sufficient emulsifying and solubilizing effects are not attained because of too high hydrophilcity and desired penetrativity is not obtained because of too large molecules. In the above general formula (1), n is preferably 0 or an integer of 1 or more, giving an average of usually 1–3.

Generally, (m+n+p) is an integer, the average thereof being in the range of 3–81, preferably 3–71, more preferably 3–41. If it exceeds 81, sufficient emulsifying and solubilizing effects are not attained because of too high hydrophilcity and desired penetrativity is not obtained because of too large molecules. The ratio (m+p)/(m+n+p) is usually at least 0.5, preferably 0.7–0.99. The ratio less than 0.5 results in poor emulsifying effects. The part of $\{(C_2H_4O)_m/(AO)_n\}$ may be block addition [in the order of $(C_2H_4O)_m$ and then $(AO)_n$] or random addition. Preferred is block addition.

Weight-average molecular weight (Mw) of the aliphatic alcohol alkylene oxide adduct (A) obtained in the invention (I) is preferably 261–5,000, particularly 300–1,200. When it is 261–5,000, surface activities, such as penetrating power, are particularly good and preferred. [Measurement of molecular weight is according to gel permeation chromatography (GPC), hereinafter these are defined as the same.]

It is necessary that the ratio Mw/Mn of Mw to number-average molecular weight (Mn) of (A) satisfies the following relation (2) or (3).

$$Mw/Mn \leq 0.030 \times Ln(v)+1.010 \text{ (in case of } v<10) \quad (2)$$

$$Mw/Mn \leq -0.026 \times Ln(v)+1.139 \text{ (in case of } v \geq 10) \quad (3)$$

In these relations, Ln(v) represents natural logarithm of v, and v represents the average number of addition moles of alkylene oxide (b1) added per 1 mole of aliphatic alcohol (a1), corresponding to average of the total of m, n and p which are numbers of addition moles of each alkylene oxide in the above general formula (1).

Sufficient surface activities are not attained, if the relation (2) or (3) is not satisfied, namely when the molecular weight distribution becomes broader.

In addition, it is preferred that the ratio Mw/Mn satisfies the following relation (2') or (3').

$$Mw/Mn \leq 0.031 \times Ln(v)+1.000 \text{ (in case of } v<10) \quad (2')$$

$$Mw/Mn \leq -0.026 \times Ln(v)+1.129 \text{ (in case of } v \geq 10) \quad (3')$$

Further, when it is possible to determine a distribution constant (c) by the following equation (4) derived from the following equation (5) of Weibull distribution law, it is necessary that (c) is not more than 1.0. Preferably, c is not more than 0.9, more preferably not more than 0.7. In the equation (4), the smaller is the value of distribution constant (c), that is, the smaller is the content of unreacted aliphatic alcohol, the narrower is the molecular weight distribution.

This equation is applicable to the case where the content of unreacted aliphatic alcohol (a1) is not less than the limit of detection (e.g. 0.001% by weight); and, in the case of (A), it is applicable up to such a level of 12 moles of the average number of addition moles of alkylene oxide (b1).

Sufficient surface activities are not attained, if c exceeds 1.

$$v = c \times Ln(n_{00}/n_0) - (c-1) \times (1-n_0/n_{00}) \quad (5)$$

$$c = (v+n_0/n_{00}-1)/[Ln(n_{00}/n_0)+n_0/n_{00}-1] \quad (4)$$

In these equations, $Ln(n_{00}/n_0)$ represents natural logarithm of $(n_{00}/n_0)$, v is defined above and $n_{00}$ represents the molar number of the aliphatic alcohol (a1) used in the reaction, and $n_0$ represents the molar number of the aliphatic alcohol (a1) unreacted.

In the case of n in the general formula (1) being 0, that is, in the case where only ethylene oxide is added to aliphatic alcohol (a1), it is preferred that the ratio Mw/Mn of weight-average molecular weight (Mw) to number-average molecular weight (Mn) satisfies the following relation (6) or (7) instead of relation (2) or (3).

$$Mw/Mn \leq 0.020 \times Ln(v)+1.010 \text{ (in case of } v<10) \quad (6)$$

$$Mw/Mn \leq -0.026 \times Ln(v)+1.116 \text{ (in case of } v \geq 10) \quad (7)$$

In the above, v represents the average number of addition moles of ethylene oxide (b1) added per 1 mole of aliphatic alcohol (a1), corresponding to the average of (m+p) in the above general formula (1).

Sufficient surface activities are not attained, if the relation (6) or (7) is not satisfied, namely when the molecular weight distribution becomes broader.

In addition, it is preferred that the ratio Mw/Mn satisfies the following relation (6') or (7').

$$Mw/Mn \leq 0.018 \times Ln(v)+1.015 \text{ (in case of } v<10) \quad (6')$$

$$Mw/Mn \leq -0.023 \times Ln(v)+1.113 \text{ (in case of } v \geq 10) \quad (7')$$

Among surfactants comprising the aliphatic alcohol alkylene oxide adduct (A) of the present invention, preferred are ones comprising (A) whose HLB is in the range of 5–13 (particularly 6–12) and having an emulsifying index s for a mineral oil of at least 8 (particularly at least 9), in view of especially good emulsifying effects to highly hydrophobic materials. Illustrative of preferable ones are those (A), in the formula (1), $R^1$ being an aliphatic hydrocarbon group containing 10–20 carbon atoms, m being 1–3 on the average, n being 0–2 on the average, and p being 1–5 on the average. Particularly preferred are those (A), $R^1$ being an aliphatic hydrocarbon group containing 12–18 carbon atoms, m being 1–3 on the average, n being 0–1 on the average, and p being 1–3 on the average. In the above and hereinafter, HLB means Griffin's HLB according to the following equation (8).

$$\text{Griffin's } HLB = (\text{Molecular weight of EO moieties in the surfactant/Molecular weight of the surfactant}) \times 20 \quad (8)$$

Herein, said emulsifying index s for a mineral oil, in case of using the surfactant of this invention as an emulsifier, is measured in accordance with the following method.

Three parts by weight of an emulsifier comprising a nonionic surfactant is blended with 97 parts by weight of a mineral oil having an aniline point of 70° C. and a viscosity of 15–25 mPa.s at 25° C.; and 5 parts by weight of the blend is thrown into a 100 ml measuring cylinder with a cap charged with 95 parts by weight of deionized water temperature-conditioned to 25° C. Then the measuring cylinder is shaken 20 times up and down, and is allowed to stand at 25° C. Upon observing emulsified state after 60 minutes, emulsifying index s is expressed according to grades evaluated on the basis below.

10: the state of being wholly emulsified homogeneously.
9: the whole being milky white, with a partly separated oil layer (less than 2 mm).
8: the whole being milky white, with a partly separated oil layer (2 mm or more, less than 5 mm).
7: the whole being milky white, with a partly separated oil layer (5 mm or more, less than 8 mm).
6: the whole being milky white, with a partly separated oil layer (8 mm or more, less than 10 mm).
5: the whole being milky white, with a partly separated oil layer (10 mm or more, less than 13 mm).
4: the oil layer being almost separated (13 mm or more), the oil layer being milky white, with a sign of transparency at the bottom of the aqueous layer.
3: the oil layer being almost separated (13 mm or more), the oil layer being milky white, with a sign of transparency at the lower half of the aqueous layer.
2: the oil layer being almost separated (13 mm or more), the oil layer being milky white, the whole aqueous layer being almost transparent.
1: being fully separated, both the oil layer and the aqueous layer being almost transparent.

Besides, among surfactants comprising (A) of this invention, preferred are ones comprising (A) whose HLB is in the range of 11–19 (particularly 12–18) and having an emulsifying index t for an oxidized polyethylene wax of at least 8 (particularly at least 9), in view of especially good emulsifying effects to highly hydrophilic materials. Illustrative of preferable ones are those (A), in the formula (1), $R^1$ being an aliphatic hydrocarbon group containing 10–20 carbon atoms, m being 1–4 on the average, n being 0–3 on the average, and p being 5–20 on the average. Particularly preferred are those (A), $R^1$ being an aliphatic hydrocarbon group containing 12–18 carbon atoms, m being 1–3 on the average, n being 1–2 on the average, and p being 5–15 on the average.

Herein, said emulsifying index t for an oxidized polyethylene wax, in case of using the surfactant of this invention as an emulsifier, is measured in accordance with the following method.

Together with ten stainless beads, 40 parts by weight of an oxidized polyethylene wax having a weight-average molecular weight of 9000–10000 and an acid number of 22–24, 11 parts of emulsifier, 0.5 parts of potassium hydrocarbon and 48.5 parts of deionized water are charged into a stainless pressure vessel, which is then sealed with nitrogen and is shaken thereafter for 30 minutes at 140° C. under pressure of 2–3 $kgf/cm^2$ to emulsify them. A state of 1% aqueous dilute liquid of the emulsified product thus obtained is expressed according to grades evaluated on the basis below. Particle size is measured, diluting the emulsified product with water to 1% by weight and using a particle size distribution measuring device of laser diffraction scattering type (For example, LA-700, produced by Horiba-Seisakusho).

10: an emulsion having an average particle size of less than 0.2 μm.
9: an emulsion having an average particle size of 0.2 μm or more, less than 0.3 μm. 8: an emulsion having an average particle size of 0.3 μm or more, less than 0.5 μm.
7: an emulsion having an average particle size of 0.5 μm or more, less than 0.6 μm.
6: an emulsion having an average particle size of 0.6 μm or more, less than 1.0 μm.
5: an emulsion having an average particle size of 1.0 μm or more and a UV (750 nm) transmission of 1% by weight aqueous solution of at least 30%.
4: an emulsion having an average particle size of 1.0 μm or more and a UV (750 nm) transmission of 1% by weight aqueous solution of less than 30%.
3: paste of high viscosity
2: insufficient emulsification causing cohesive failure.
1: each component being separated.

Further, among surfactants comprising said alkylene oxide adduct (A) of the invention, preferred are ones comprising (A) having an HLB in the range of 7–15 (particularly 8–14), a solidifying point of (A) satisfying the following relation (9), in view of easy handling at lower temperature as compared with conventional aliphatic alcohol alkylene oxide adducts, along with good emulsifying effects. Emulsifying effects are especially good when HLB is in the range of 8–14. Illustrative of preferable ones are those (A), in the formula (1), $R^1$ being an aliphatic hydrocarbon group containing 10–20 carbon atoms, m being 1–4 on the average, n being 1–3 on the average, and p being 1–20 on the average. Particularly preferred are those (A), $R^1$ being an aliphatic hydrocarbon group containing 12–18 carbon atoms, m being 1–3 on the average, n being 1–3 on the average, and p being 2–16 on the average.

$$1.61x-102 \leq y \leq 1.61x-92 \tag{9}$$

Herein, x represents % by weight of units represented by $C_2H_4O$ in the general formula (1) formed by addition of EO, and y represents the solidifying point (° C.) of the aliphatic alcohol alkylene oxide adduct (A).

It is further preferred that the solidifying point y satisfies the following relation (9').

$$1.61x-100 \leq y \leq 1.61x-95 \tag{9'}$$

Among surfactants comprising the aliphatic alcohol alkylene oxide adduct (A) of this invention, preferred are ones comprising (A) whose HLB is in the range of 7–15 (particularly 8–14) and having a detergency index for artificial soils supported on a slide glass [standardizing detergency of nonylphenol ethylene oxide 9.5 moles adduct as 100] of at least 100 (particularly at least 102), in view of excellent detergency for hard surfaces such as metals and tablewares and clothes. Illustrative of preferable ones are those (A), in the formula (1), R satisfies being an aliphatic hydrocarbon group containing 10–20 carbon atoms, m being 1–4 on the average, n being 1–3 on the average, and p being 3–15 on the average. Particularly preferred are those (A), R satisfies being an aliphatic hydrocarbon group containing 12–18 carbon atoms, m being 1–3 on the average, n being 1–3 on the average, and p being 5–10 on the average.

Herein, said detergency index is measured in accordance with the following method. Hereinafter, % means % by weight, unless otherwise specified.

| <<Formulation of Detergent Liquor>> | |
|---|---|
| Nonionic surfactant | 5 % |
| Na laurylbenzenesulfonate | 10 % |
| Ethanol | 5 % |
| Urea | 5 % |
| Water | 75 % |
| Total | 100 % |

Detergency test is carried out in accordance with Leenerts method (JIS K3370), using a detergent liquor formulated according to the above formulation. Six sheets of slide glasses are used as a pair of substrates for soils, and a chloroform solution of artificial soils having the following composition is used as soil components. The slide glass coated with the artificial soils is washed with an aqueous solution of 0.15% concentration of the detergent liquor as a wash liquid; and a detergency is determined according to the following equation, and a detergency index is represented as an index making detergency of nonylphenol ethylene oxide 9.5 moles adduct as 100.

| <<Composition of Artificial Dirt Components>> | |
|---|---|
| Tallow | 16.6 % |
| Soybean oil | 16.6 % |
| Monoolein | 0.4 % |
| Oil red | 0.2 % |
| Chloroform | 66.2 % |
| Total | 100 % |

Detergency (%) = 100 × [Amount of soils (g) before washing – Amount of soils (g) after washing]/Amount of soils (g) before washing Among surfactants comprising the aliphatic alcohol alkylene oxide adduct (A) of the invention, preferred are ones comprising (A) whose IILB is in the range of 10–14 (particularly 11–13) and having a viscosity index of 5% aqueous solution [standardizing viscosity of nonylphenol ethylene oxide 8.5 moles adduct as 100) of at least 50

(particularly at least 70), in view of high thickening function and usefulness as a thickener. Illustrative of preferable ones are those (A), in the formula (1), $R^1$ being an aliphatic hydrocarbon group containing 10–20 carbon atoms, m being 1–4 on the average, n being 0–3 on the average, and p being 1–10 on the average. Particularly preferred are those (A), $R^1$ being an aliphatic hydrocarbon group containing 12–18 carbon atoms, m being 1–3 on the average, n being 0–1 on the average, and p being 3–7 on the average.

Herein, said viscosity index is measured in accordance with the following method.

A 5% aqueous solution of a nonionic surfactant is prepared, and its viscosity is measured at 25° C., with a Brookfield type viscometer, using a rotor No.3, at 40 rpm; and a viscosity index is represented as an index making viscosity of 5% aqueous solution of nonylphenol ethylene oxide 8.5 moles adduct as 100.

In applying nonionic surfactants of the present invention for their uses, there may be formulated other nonionic surfactants, anionic surfactants, cationic surfactants and amphoteric surfactants. To be concrete, nonionic surfactants include, for example, polyoxyalkylene ($C_{2-8}$) aliphatic ($C_{8-24}$) alcohol (degree of polymerization=1–100) other than the present invention, higher fatty acid ($C_{8-24}$) esters of polyoxyalkylene ($C_{2-8}$, degree of polymerization=1–100) [e.g. polyethylene glycol monostearate (degree of polymerization=20), polyethylene glycol distearate (degree of polymerization=30), etc.], fatty acid ($C_{8-24}$) esters of polyhydric (di- to deca- or more hydric) alcohol [e.g. glycerol monostearate, ethylene glycol monostearate, sorbitan monolaurate, etc.], fatty acid ($C_{8-24}$) esters of polyoxyalkylene ($C_{2-8}$, degree of polymerization=1–100) adduct of polyhydric (di- to deca- or more hydric) alcohol [e.g. polyoxyethylene (degree of polymerization=10) sorbitan monolaurate, polyoxyethylene (degree of polymerization=50) dioleic methyl glycoside, etc.], fatty acid alkanolamides [e.g. 1:1 Mole coconut oil fatty acid diethanolamide, 1:1 Mole lauroyl diethanolamide, etc.], polyoxyalkylene ($C_{2-8}$, degree of polymerization=1–100) alkyl($C_{1-22}$)-phenyl ethers, polyoxyalkylene($C_{2-8}$, degree of polymerization= 1–100)-alkyl($C_{8-24}$)amino ethers, and alkyl ($C_{8-24}$) dialkyl ($C_{1-6}$) amine oxides [e.g. lauryldimethylamine oxide etc.].

Examples of anionic surfactants include $C_{8-24}$ hydrocarbon ether carboxylic acids or salts thereof [e.g. sodium lauryl polyoxyethylene (degree of polymerization=1–100) ether acetate, disodium lauryl polyoxyethylene (degree of polymerization=1–100) sulfosuccinate, etc.], salts of $C_{8-24}$ hydrocarbon sulfates [e.g. sodium lauryl sulfate, sodium lauryl polyoxyethylene (degree of polymerization=1–100) ether sulfate, triethanolamine salt of lauryl polyoxyethylene (degree of polymerization=1–100) ether sulfate, sodium coconut oil fatty acid monoethanolamide polyoxyethylene (degree of polymerization=1–100) ether sulfate, etc.], salts of $C_{8-24}$ hydrocarbon sulfonates [e.g. sodium dodecylbenzene sulfonate etc.], and salts of $C_{8-24}$ hydrocarbon phosphate esters [e.g. sodium lauryl phosphate, sodium lauryl polyoxyethylene (degree of polymerization=1–100) ether phosphate etc.], salts of fatty acids [e.g. sodium laurate, triethanolamine laurate etc.], salts of acylated amino acids [e.g. sodium coconut oil fatty acid methyltaurate, sodium coconut oil fatty acid sarcosinate, triethanolamine coconut oil fatty acid sarcosinate, triethanolamine N-coconut oil-fatty acid-L-glutamate, sodium N-coconut oil fatty acid-L-glutamate, sodium lauroyl methyl-β-alanine, etc.] and others [e.g. lauroylethanolamide sulfosuccinate disodium polyoxyethylene (degree of polymerization=1–100) etc.].

Examples of cationic surfactants include quaternary ammonium salts type [e.g. stearyl trimethyl ammonium chloride, behenyl trimethyl ammonium chloride, distearyl dimethyl ammonium chloride, lanolin fatty acid aminopropyl ethyl dimethyl ammonium ethylsulfate, etc.] and amine salts type [e.g. diethylaminoethylamide lactate stearate, dilaurylamine hydrochloride, oleylamine lactate, etc.]. Exemplary of amphoteric surfactants include betaine type amphoteric surfactants [e.g. coconut oil fatty acid amidopropyl dimethyl betaine, lauryl dimethyl betaine, 2-alkyl-N-carboxymethyl-N-hydroxyethyl imidazolinium betaine, lauryl hydroxysulfobetaine, sodium lauroylamidoethyl hydroxyethylcarboxymethylbetaine hydroxypropylphosphate, etc.], amino acid type amphoteric surfactants [e.g. sodium β-laurylaminopropionate etc.].

Nonionic surfactants of this invention exhibit excellent performances, with respect to emulsifiability, emulsion stability, low foaming properties and the like, when used in uses, for example, emulsifiers (I), such as emulsifiers for metal working, emulsifiers for agrochemical emulsions, emulsifiers for cosmetics, emulsifiers for aqueous coatings and emulsifiers for emulsion polymerization. To be concrete, they can be used as emulsifiers for producing O/W or W/O emulsions of mineral oils; vegetable oils, e.g. castor oil, soybean oil and olive oil; animal oils and fats, such as tallow and egg yolk oil; monomers, such as styrene and acrylic esters, to which their uses are not limited.

Besides uses as emulsifiers (I), nonionic surfactants of the invention are also useful for various surfactant uses as dispersants (J) of agents for paper, such as pigments and metal salts of fatty acids; solubilizers (K) of perfumes and the like; detergents (L) as household detergents such as detergents for clothes and dish-washing detergents, and as industrial detergents such as detergents for machinery metals; and penetrating agents (M) or wetting agents (N).

In case using said aliphatic alcohol alkylene oxide adduct (A) of the present invention as emulsifiers (I), dispersants (J) or solubilizers (K), it is preferred that p in the formula (1) is such an integer of 2–40 on the average. If it exceeds 40, the resulting product is too hydrophylic and unpreferable as emulsifier, dispersant or solubilizer. Besides, Mw of (A), when used in the above uses, is preferably 261–2,000, more preferably 270–1,500.

(II) Process for Producing Nonionic Surfactant

It is preferred that said aliphatic alcohol alkylene oxide adduct (A) of the present invention is produced by the process (II) of this invention.

In the process (II) of the invention, an aliphatic alcohol alkylene oxide adduct (e) is one obtainable by adding 1–2.5 moles on the average of an alkylene oxide (b2) to an aliphatic alcohol (a2) in the presence of a catalyst (d) providing an adduct having a distribution constant c' of 1.0 or less as determined by the following equation (4') derived from Weibull distribution law. Through addition-reaction of an alkylene oxide (b3) containing at least two carbon atoms to this adduct (e) in the presence of an alkaline catalyst (f), an aliphatic alcohol alkylene oxide adduct of narrow molecular weight distribution is attained.

$$c'=(v'+n_0'/n_{00}'-1)/[\mathrm{Ln}(n_{00}'/n_0')+n_0'/n_{00}'-1] \tag{4'}$$

Herein, v' represents the average addition molar number of the alkylene oxides (b2) and (b3) added per 1 mole of the aliphatic alcohol (a2), $n_{00}'$ represents the molar number of the aliphatic alcohol (a2) used in the reaction, and $n_0'$ represents the molar number of the aliphatic alcohol (a2) unreacted.

Aliphatic alcohols (a2) are alcohols containing usually 1–24 (preferably 8–24, particularly 12–18) carbon atoms and may be natural alcohols or synthetic alcohols (such as Ziegler alcohols and oxo alcohols). Among these, alcohols containing 8–24 carbon atoms include the same ones as (a1). Aliphatic alcohols containing 1–7 carbon atoms include, for example, saturated aliphatic alcohols, such as methanol, ethanol, propanol, butanol, pentyl alcohol, hexyl alcohol and heptyl alcohol; unsaturated aliphatic alcohols, such as propenyl alcohol, butenyl alcohol and pentenyl alcohol; and cycloaliphatic alcohols, such as methylcyclohexyl alcohol. There may be used one or two or more of these. Among these aliphatic alcohols, preferred are primary or secondary ones and more preferred are primary ones. Besides, the alkyl group moiety may be linear or branched. Particularly preferred are dodecyl alcohol, tridecyl alcohol, tetradecyl alcohol, hexadecyl alcohol and octadecyl alcohol.

As alkylene oxides (b2) and (b3), there may be mentioned alkylene oxides containing at least 2, preferably 2–8, particularly 2–3 carbon atoms. Illstrative examples include EO, PO, 1,2- or 2,3-butylene oxide, tetrahydrofran, styrene oxide and the like, and two or more may be used together. When two or more are used, they may be added block-wise or added random-wise. Among these, preferred are EO and PO.

As the catalyst (d), used is one providing a distribution constant c' of the resulting alkylene oxide adduct of 1.0 or less. Preferred is one providing c' of 0.7 or less, more preferably c' of 0.45 or less.

Catalysts providing c' of 1.0 or less include, for example, perhalogenoic acids or salts thereof, sulfuric acid or salts thereof, phosphoric acid or salts thereof and nitric acid or salts thereof. Metals in the case of forming salts are not particularly restricted, but preferably metals other than alkali metals and preferred are divalent or trivalent metals. Preferable of these metals are Mg, Ca, Sr, Ba, Zn, Co, Ni, Cu and Al; more preferred are Mg, Zn, Ca, Sr, Ba and Al, particularly Mg, Zn and Al. Halogens of perhalogenoic acids or salts thereof include chlorine, bromine and iodine, and preferred is chlorine. Thus, preferred as (d) are divalent or trivalent metal perchlorates, and more preferred are perchlorates of metal selected from the group consisting of Mg, Zn and Al. Besides, divalent or trivalent metal alcoholate may be used in combination. The amount of the metal alcoholate used together is 20–200 parts by weight per 100 parts by weight of (d). As alkyl groups of metal alcoholates, there may be mentioned lower alkyl groups (containing 1–4 carbon atoms) easy to be distilled off as alcohols, or alkyl groups of the same composition as the raw material aliphatic alcohols. Though one kind of these catalysts may be used alone, it is preferred to use two or more catalysts in conjunction [for example, magnesium perchlorate/magnesium sulfate heptahydrate=95/5–50/50, magnesium perchlorate/aluminum perchlorate=99/1–30/70 (all weight ratio)].

From the reaction rate and economical point of view, preferable amount of catalyst (d) is 0.001–1 part by weight per 100 parts by weight of the total of (a2) and (b2). More preferably it is 0.003–0.8 part by weight, particularly 0.005–0.5 part by weight.

Catalyst used in adding an alkylene oxide (b3) to an alkylene oxide adduct (e) obtained by adding (b2) to (a2) is an alkaline catalyst (f). Alkaline catalysts (f) include hydroxides of alkali metals and alkaline earth metals, for example, lithium hydroxide, sodium hydroxide, potassium hydroxide, cesium hydroxide, magnesium hydroxide, calcium hydroxide and barium hydroxide; among which more preferred are potassium hydroxide and cesium hydroxide.

From the reaction rate and economical point of view, preferable amount of catalyst (f) is 0.0001–1 part by weight per 100 parts by weight of the total of (e) and (b3). More preferably it is 0.001–0.8 part by weight.

As to reaction conditions in the case of reacting (a2) with (b2), there may be mentioned methods comprising mixing (a2) with (d), carrying out nitrogen substitution, thereafter introducing (b2) at a temperature of 80–200° C. under pressure of −0.8–5 kgf/cm$^2$ to a prescribed amount of (b2), followed by carrying out aging at a temperature of 80–200° C. until the pressure within the reaction system reaches equilibrium.

To an alkylene oxide adduct (e) thus obtained, is added an alkaline catalyst (f), followed by reacting an alkylene oxide (b3) in the same manner as above to obtain an aimed aliphatic alcohol alkylene oxide adduct.

After termination of polymerization according to this invention, the resulting aliphatic alcohol alkylene oxide adduct may be used as such or through adjusting pH for various applications. If desired, the catalyst can be removed from the polymerized product, through adsorption treatment with an adsorbent, such as "Kyowaad 600" (an adsorbent of aluminum silicate type, produced by Kyowa Chemical Ind.), followed by filtration operation. In this case, the time required for filtration operation can optionally reduced by using a filter aid of diatomaceous earth type (such as "Radiolite", produced by Showa Chemical Ind.). Besides, the alkaline catalyst may be neutralized with a hydroxycarboxylic acid (such as lactic acid) as written in JP Patent Lay-open No. 112931/1981 and JP Patent Publication No. 53417/1990.

Since aliphatic alcohol alkylene oxide adducts obtained by the process (II) of the invention are of lower content of unreacted aliphatic alcohol, they can be used for the purpose of improving odor as intermediates for anionic surfactants of low odor, such as sulfated products and carboxymethylated products. They are of course useful in the above-mentioned uses, such as emulsifiers and dispersants.

(III) Anionic Surfactant

In another aspect of the present invention, provided is an anionic surfactant obtainable by anionization of an aliphatic alcohol alkylene oxide adduct (A'), said (A') being directly produced by adding an alkylene oxide (b1) to an aliphatic alcohol (a1) and satisfying the following (ii'), (iii') and (iv).
(ii') The ratio Mw/Mn of a weight-average molecular weight (Mw) to a number-average molecular weight (Mn) satisfies the following relation (2') or (3').

$$Mw/Mn \leq 0.030 \times Ln(v'') + 1.010 \text{ (in case of } v'' < 10) \qquad (2')$$

$$Mw/Mn \leq -0.026 \times Ln(v'') + 1.139 \text{ (in case of } v'' \geq 10) \qquad (3')$$

Herein, v" represents the average of (m'+n'+p') in the following general formula (1').
(iii') A distribution constant c", determined by the following equation (4"), is 1.0 or less.

$$c'' = (v'' + n_0/n_{00} - 1)/[Ln(n_{00}/n_0) + n_0/n_{00} - 1] \qquad (4'')$$

Herein, v" is the same in the above. This is required only in the case of v" up to 12, as described above. The $n_{00}$ represents the molar number of the aliphatic alcohol (a1) used in the reaction, and $n_0$ represents the molar number of the aliphatic alcohol (a1) unreacted.
(iv) It comprises one compound or a mixture of two or more thereof, represented by the following general formula (1'):

$$R^1O\text{—}[(C_2H_4O)_{m'}/(AO)_{n'}]\text{—}(C_2H_4O)_{p'}\text{—}H \qquad (1')$$

Herein, R$^1$ is an aliphatic hydrocarbon group containing 8–24 carbon atoms or a cycloaliphatic hydrocarbon group containing 8–24 carbon atoms; A is an alkylene group containing at least 3 carbon atoms; m' is 0 or an integer of 1 or more, the average thereof being in the range of 0–5, n' is 0 or an integer of 1 or more, the average thereof being in the range of 0–5, p' is 0 or an integer of 1 or more, the average thereof being in the range of 0–10, (m'+n'+p') is an integer, the average thereof being in the range of 1–20, and average of (m'+p')/(m'+n'+p') is at least 0.5. In case of m'≠0 and n'≠0, $[(C_2H_4O)_m'/(AO)_n']$ represents block addition or random addition.

The general formula (1) and the general formula (1') are different with respect to the values of m, n and p and m', n' and p', though $R^1$ and A are the same. That is, m' in the general formula (1') is 0 or an integer of 1 or more, the average thereof being in the range of 0–5; while m in the general formula (1) is 0 or an integer of 1 or more, the average thereof being in the range of 0–4. In the general formula (1'), n' is 0 or an integer of 1 or more, the average thereof being in the range of 0–5; whereas n in the general formula (1) is 0 or an integer of 1 or more, the average thereof being in the range of 0–3. In the general formula (1'), p' is 0 or an integer of 1 or more, the average thereof being in the range of 1–10; while p in the general formula (1) is 0 or an integer of 1 or more, the average thereof being in the range of 1–80. In the general formula (1'), (m'+n'+p') is an integer, the average thereof being in the range of 1–20; whereas (m+n+p) in the general formula (1) is an integer, the average thereof being in the range of 3–81. With respect to (m+p)/(m+n+p), the both are equally at least 0.5 on average.

As aliphatic alcohol alkylene oxide adducts (A') satisfying (ii'), (iii') and (iv), there may be used alkylene oxide adducts after termination of the first step before using an alkaline catalyst or alkylene oxide adducts after termination of the second step, in the above-described production method of aliphatic alcohol alkylene oxide adduct comprising two steps, as far as they are ones satisfying (ii'), (iii') and (iv).

Methods for anionizing an aliphatic alcohol alkylene oxide adduct (A') satisfying (ii'), (iii') and (iv) are not particularly restricted, as far as the terminal hydroxyl group is anionized, and include, for example, sulfation, phosphation, sulfosuccination and carboxyetherification.

As sulfation, there can be mentioned a method by sulfating the resulting aliphatic alcohol alkylene oxide adduct (A') as such and then neutralizing with an alkali such as sodium hydroxide. Concretely, there may be mentioned, for instance, (a) method by using chlorosulfonic acid, (b) method by using sulfan, (c) method by using sulfamic acid and (d) method by using sulfuric acid. Sulfan of (b) is used diluted with dry nitrogen or the like.

Reaction temperature is usually 0–70° C., preferably 10–50° C. in the cases of (a) and (b). It is usually 50–150° C., preferably 60–130° C. in the cases of (c) and (d). Reaction time, which may vary depending on reaction temperature, is generally 0.1–10 hours, preferably 0.5–5 hours. Molar ratio of (A') to the above sulfating agent is usually 1.0:1.2–1.0:0.8, preferably 1.0:1.1–1.0:0.9.

Reaction manners, in any cases of (a)–(d), include both continuous reaction and batch-wise reaction.

End point of sulfating reaction is such a point that the acid value (AV) represented by 56100/(molecular weight of sulfated product) reaches 90–110%, preferably 95–105%, of the theoretical value.

Besides, the end point, which may be confirmed through measuring the amount of combined sulfuric acid, is such a point that the amount of combined sulfuric acid represented by (80×100)/(molecular weight of sulfated product) reaches 90–110%, preferably 95–105%, of the theoretical value.

Phosphation can be carried out by phosphating the resulting aliphatic alcohol alkylene oxide adduct (A') with an phosphating agent, such as phosphoric acid, polyphosphoric acid, phosphoric anhydride, phosphorus oxychloride or the like, and then neutralizing with NaOH, KOH, an amine or the like. Phosphation is same as phosphoric esterification, and forms monoester, diester and the like, all these are included within the invention.

Reaction of (A') with phosphoric anhydride is carried out at a reaction temperature of usually 30–150° C., preferably 60–130° C. within an atmosphere of nitrogen to obtain diphosphoric ester of (A'), followed by hydrolyzing with water equimolar of phosphoric anhydride to thereby obtain monophosphoric ester of (A'). Reaction time, which may vary depending on reaction temperature, is generally 1–10 hours, preferably 2–5 hours. Molar ratio of (A') to the phosphoric anhydride is usually 2.0:1.15–2.0:0.85, preferably 2.0:1.05–2.0:0.95 in the case of monophosphoric ester and usually 1.0:0.4–1.0:0.6, preferably 1.0:0.45–1.0:0.55 in the case of diphosphoric ester.

End point of phosphating reaction is such a point that the acid value (AV) represented by 56100/(molecular weight of esterified product) reaches 90–110%, preferably 95–105%, of the theoretical value. Thereafter, the product is neutralized with an aqueous solution of an alkali such as NaOH or an amine to obtain an objective composition. Degree of neutralization may be optionally selected.

Sulfosuccination is a method by two step reaction processes, comprising the step of reacting (A') with maleic anhydride (hereinafter referred to as MA) to obtain a monoester and the step of sulfonating it in the presence of water with a sulfite or an acid sulfite.

Reaction of (A') with MA is carried out at a reaction temperature of usually 50–100° C., preferably 60–90° C. within an atmosphere of nitrogen to obtain a MA monoester of (A'). In case where MA is added in an excess amount, MA is removed under reduced pressure after termination of the monoesterification reaction. Molar ratio of (A') to MA is usually 1.0:0.9–1.0:1.1, preferably 1.0:0.95–1.0:1.05.

End point of monoesterification is such a point that an acid number represented by 56100/(molecular weight of the esterified product) reaches 90–110% of the theoretical value, preferably 95–105%.

Subsequently, the resulting monoesterified product is sulfonated with a sulfite or an acid sulfite. Sulfites include, for example, alkali metal salts, such as sodium sulfite and potassium sulfite, alkaline earth metal salts, such as magnesium sulfite, and ammonium salts, such as ammonium sulfite. Acid sulfites include hydrogen sulfites, such as sodium hydrogen sulfite, potassium hydrogen sulfite, ammonium hydrogen sulfite and magnesium hydrogen sulfite. Sulfonation can be carried out by reacting the esterified product with a sulfite or an acid sulfite in the presence of water. Molar ratio of the monoesterified product to a sulfite or an acid sulfite is usually 1.0:0.9–1.0:1.1, preferably 1.0:0.95–1.0:1.05. Reaction temperature is usually 30–90° C., preferably 40–80° C. The reaction is usually carried out within an atmosphere of nitrogen. Reaction period, which may vary depending upon the reaction temperature, is generally 1–10 hours, preferably 2–5 hours.

End point of sulfonation is such a point that a combined surfuric acid amount represented by (80×100)/molecular weight of the sulfonated product reaches 90–110%, preferably 95–105% of the theoretical value. After sulfonation is terminated, pH is adjusted to neutralize with an organic acid such as citric acid or an alkanolamine such as triethanolamine. Carboxyetherification can be carried out, for instance, through condensation reaction of the resulting aliphatic alcohol alkylene oxide adduct (A') with a mono-halosubstituted lower carboxylic acid salt, such as a monochloroacetate, a monobromoacetate, a monochloropropionate, a monobromopropionate or the like (preferably a monochloroacetate, particularly sodium monochloroacetate), in the presence of a caustic alkali and optionally a solvent.

Reaction of (A') with sodium monochloroacetate can be carried out, for example, in a molar ratio of (A') to sodium monochloroacetate of usually 1.0:0.90–1.0:1.60 preferably 0:0.95–1.0:1.50, at a reaction temperature of usually 30–100° C. preferably 40–70° C., within an atmosphere of nitrogen, using a solvent such as toluene and adding sodium hydroxide gradually. Then, purification processes such as water washing and separation are gone through to obtain a carboxyetherified product of the aliphatic alcohol alkylene oxide adduct. Thereafter, water is added thereto to obtain an aqueous solution of the carboxyetherified product of the aliphatic alcohol alkylene oxide adduct.

Degree of etherification in carboxyetherification can be measured with liquid chromatography under the following conditions.

| Measurement conditions of liquid chromatography | |
|---|---|
| Colmun: | ODS type, 6 mm φ × 15 cm |
| Colmun temperature: | 35° C. |
| Elutant: | methanol/water = 90/10 |
| Flow rate: | 0.8 ml/min. |
| Sample concentration: | 10% |
| Pour: | 30 μl |

End point is such a point that a degree of etherification reaches at least 90%, preferably at least 95%.

Kinds of anionization as described above may be variously selected, and there can be used different types depending upon uses of the resulting anionic surfactants. Among anionized products, preferred are the above-mentioned four types.

Concrete examples of preferable anionic surfactants include anionized products of (A') of the general formula (1), wherein $R^1$ is an aliphatic hydrocarbon group containing 8–18 carbon atoms, m' is 0–2 on the average, n' is 0–2 on the average, p' is 1–3 on the average, and m'+n'+p' is 1–6 on the average; and particularly preferred are anionized products of (A'), $R^1$ being an aliphatic hydrocarbon group containing 8–14 carbon atoms and m'+n'+p' being 1–5 on the average.

Anionic surfactants, obtain by anionizing (A') satisfying (ii'), (iii') and (iv) according to the above methods, exhibit excellent forming properties and detergency. Besides, since aliphatic alcohol alkylene oxide adduct (A') satisfying (ii'), (iii') and (iv) contains the raw material aliphatic alcohols only in a small amount, there can be attained ones of less skin irritation to human bodies owing to lower content of anionized products of aliphatic alcohols. In addition, odor is also bettered. Moreover, phosphated products, sulfosuccinated products and carboxyetherified products heretofore have had problems in long-term storage stablity at lower temperature and higher temperature (particularly misting or solidification at lower temperature), while products according to the present invention have remarkably improved stability. Besides, anionic surfactants of this invention, having surface activities, such as penetrating properties in addition to detergency and forming properties as above, are particularly useful as detergents, for example, shampoo, detergent for dishes, detergent for rigid surfaces such as metals.

In applying anionic surfactants thus obtained for detergents and other uses, there may be formulated other nonionic surfactants, anionic surfactants, cationic surfactants and amphoteric surfactants. To be concrete, there can be mentioned those described above with respect to nonionic surfactants.

(IV) Detergent Compositions

In addition to using the anionic surfactant of the invention alone, it may be made into a detergent composition, preferably by blending a nonionic surfactant and/or an amphoteric surfactant. Illustrative of nonionic surfactants and amphoteric surfactants are those mentioned above regarding nonionic surfactants. Amounts of surfactant active ingredients formulated within compositions are, as solid content, 3–60% preferably 5–50% of the anionic surfactant of the invention, preferably 3–60% particularly 5–50% of a nonionic surfactant and preferably 1–50% particularly 2–30% of an amphoteric surfactant.

Besides, additives known heretofore can be formulated in the detergent compositions. There may be used together as such additives, humectants, such as glycerol and sodium pyrrolidone-carboxylate; high molecular weight compounds used as conditioners, such as cationized cellulose, cationized guar gum, polyethyleneglycol, sodium polyacrylate, hydroxyethyl cellulose and protein derivatives respectively having a weight-average molecular weight of 500–5,000,000; silicones, such as dimethylpolysiloxane, modified silicones having various organic groups introduced into a part of methyl groups of dimethylpolysiloxane and cyclic dimethylsiloxane; chelating agents, such as sodium ethylenediamine-tetraacetate and sodium 1-hydroxyethane-1,1-diphosphonate; lower alcohols, such as ethanol, propylene glycol and dipropylene glycol; perfumes, colorants, preservatives, ultraviolet absorbers and water.

Forms of detergent compositions, including usually liquids, pastes, solids, powders and the like, are not particularly restricted, but liquids and pastes are preferred in view of handiness. In case of liquid and paste shampoos, for example, are used the anionic surfactant of the invention in an amount of 5–30% by weight, the total of surfactants in the range of 5–50% by weight, preferably 10–30% by weight, high molecular weight compounds and silicones in an amount of 0–5% by weight, humectants, chelating agents and lower alcohols in an amount of 0–10% by weight and water in an amount of 35–95% by weight.

EXAMPLES

This invention is further explained by Examples below, but the invention is not limited to these. Parts represent parts by weight and % represents % by weight.

Measurements of molecular weights in Examples 1–16 and Comparative Examples 1–13 are carried out through gelpermeation chromatography (hereinafter referred to as GPC) below.

<<Measurement conditions-1 of GPC>>

Kind of Machine: HLC-8120 (produced by Tosoh Corp.)
Column: TSK gels SuperH4000, 3000 and 2000 (all produced by Tosoh Corp.)
Column temperature: 40° C.; Detector: RI;
Solvent: tetrahydrofuran; Flow rate: 0.6 ml/min.;
Sample concentration: 0.25 %; Pour: 10 μl ;
Standard: polyoxyethylene glycol (TSK STANDARD POLYETHYLENE OXIDE, produced by Tosoh Corp.)
Data processor: SC-8020 (produced by Tosoh Corp.)

Measurements of concentration of unreacted aliphatic alcohol in Examples 1–16 and Comparative Examples 1–13 are carried out through gas chromatography (hereinafter referred to as GC) below.

| <<Measurement conditions of GC>> |
|---|
| Kind of Machine: Gas chromatograph GC-14B (produced by Shimadzu Corp.) |
| Detector: FID |
| Column: Glass column (inner diameter = about 3 mm, length = about 2 m) |
| Column packing material: Silicone GE SE-30 5% |
| Column temperature: raised from 90° C. to 280° C. |
| Heat-up rate: 4° C./min.; Carrier gas: nitrogen; |
| Sample: 50% acetone solution; Pour: 1 µl; |
| Determination: determined using, as an internal standard, an aliphatic alcohol containing carbon atoms less by 2 or 3 than the aliphtic alcohol used. |

Example 1

Into a stainless autoclave equipped with stirring and temperature-controlling functions, 186 parts (1 mole) of lauryl alcohol, 0.05 part of magnesium perchlorate and 0.01 part of magnesium sulfate heptahydrate were charged; and, after replacing the atmosphere within the vessel with nitrogen, dehydration was carried out for 1 hour at 120° C. under reduced pressure (about 20 mmHg). Then, 88 parts (2 moles) of EO was introduced under a gauge pressure of 1–3 kgf/cm$^2$ at 150° C. Weibull distribution constant c' of the resulting adduct was 0.42, and the amount of unreacted alcohol was 2.2% (0.032mole). To this adduct, was added 0.3 parts of potassium hydroxide, and 220 parts (5 moles) of EO was introduced under a gauge pressure of 1–3 kgf/cm$^2$ at 150° C. To the reaction product, was added 3 parts of "Kyowaad 600" (an adsorbent of aluminum silicate type, produced by Kyowa Chemical Corp.), and the catalysts were adsorbed at 90° C., followed by filtering them to obtain a nonionic surfactant (B-1) of this invention.

Upon measuring molecular weight distribution and unreacted aliphatic alcohol amount through GPC and GC, Mw/Mn was 1.045 [calculated value of the upper limit of Mw/Mn satisfying the relation (6): 1.049], and the calculated value of distribution constant c according to the equation (4) was 0.92.

Regarding Examples 2–14 and Comparative Examples 1–11, molecular weight distribution and unreacted aliphatic alcohol amount were also measured similarly through GPC and GC. The results, together with those of Example 1, are shown in Tables 1, 2 and 4.

Example 2

In the same manner as Example 1, except that 0.04 part of magnesium perchlorate and 0.01 part of aluminum perchlorate nonahydrate were used instead of 0.05 part of magnesium perchlorate (distribution constant c' of the resulting adduct being 0.38 and the amount of unreacted alcohol being 1.7%) and that 352 parts (8 moles) of EO was used instead of 220 parts of EO introduced in the presence of the alkaline catalyst, a nonionic surfactant (B-2) of this invention was obtained.

Example 3

In the same manner as Example 1, except that barium sulfate was used instead of magnesium sulfate heptahydrate (distribution constant c' of the resulting adduct being 0.32 and the amount of unreacted alcohol being 1.1%) and that 618 parts (14 moles) of EO was used instead of 220 parts of EO in the presence of the alkaline catalyst, a nonionic surfactant (B-3) of this invention was obtained.

Example 4

In the same manner as Example 1, except that 1,672 parts (38 moles) of EO was used instead of 220 parts of EO in the presence of the alkaline catalyst, a nonionic surfactant (B-4) of this invention was obtained.

Example 5

In the same manner as in Example 1, except using no magnesium sulfate heptahydrate, an EO adduct of lauryl alcohol was obtained. Distribution constant c' of the resulting adduct was 0.60, and the amount of unreacted alcohol was 4.5%. To this adduct, 1.3 parts of potassium hydroxide was added, and 116 parts (2 moles) of PO and then 176 parts (4 moles) of EO were introduced under a gauge pressure of 1–3 kgf/cm$^2$ at 130° C. The reaction product was post-treated in the same manner as in Example 1 to obtain a nonionic surfactant (A-1) of this invention.

Example 6

In the same manner as Example 5, except that 528 parts (12 moles) of EO was used instead of 176 parts of EO introduced in the presence of the alkaline catalyst, a nonionic surfactant (A-2) of this invention was obtained.

Example 7

Into the same vessel as in Example 1, 186 parts (1 mole) of lauryl alcohol, 0.05 part of magnesium perchlorate and 0.05 part of zinc perchlorate were charged; and, after replacing the atmosphere within the vessel with nitrogen, dehydration was carried out for 1 hour at 120° C. under reduced pressure (about 20 mmHg). Then, 116 parts (2 moles) of PO was introduced under a gauge pressure of 1–3 kgf/cm$^2$ at 120° C. Distribution constant c' of the resulting adduct was 0.42, and the amount of unreacted alcohol was 2.0%. To this adduct, 1.3 parts of potassium hydroxide was added, and 704 parts (16 moles) of EO was introduced under a gauge pressure of 1–3 kgf/cm$^2$ at 130° C. The reaction product was post-treated in the same manner as in Example 1 to obtain a nonionic surfactant (A-3) of this invention.

Example 8

In the same manner as in Example 1, except using 0.05 part of zinc perchlorate instead of magnesium sulfate, dehydration of lauryl alcohol was carried out. Then, 44 parts (1 mole) of EO and 58 parts (1 mole) of PO were mixed and introduced under a gauge pressure of 1–3 kgf/cm$^2$ at 120° C. Distribution constant c' of the resulting adduct was 0.34, and the amount of unreacted alcohol was 1.3%. To this adduct, 1.3 parts of potassium hydroxide was added, and 704 parts (8 mole) of EO was introduced under a gauge pressure of 1–3 kgf/cm$^2$ at 130° C. The reaction product was post-treated in the same manner as in Example 1 to obtain a nonionic surfactant (A-4) of this invention.

Example 9

In the same manner as in Example 1, except using 0.03 part of zinc sulfate instead of magnesium sulfate, an EO adduct of lauryl alcohol was obtained. Distribution constant c' of the resulting adduct was 0.38 and the amount of unreacted alcohol was 1.7%. To this adduct, 1.3 parts of potassium hydroxide was added, and 144 parts (2 moles) of 1,2-butylene oxide and then 704 parts (8 moles) of EO were introduced under a gauge pressure of 1–3 kgf/cm² at 130° C. The reaction product was post-treated in the same manner as in Example 1 to obtain a nonionic surfactant (A-5) of this invention.

Comparative Example 1

Into the same vessel as in Example 1, 186 parts (1 mole) of lauryl alcohol and 0.3 part of potassium hydroxide were charged; and after replacing the atmosphere within the vessel with nitrogen, dehydration was carried out for 1 hour at 120° C. under reduced pressure (about 20 mmHg). Then, 308 parts (7 moles) of EO was introduced under a gauge pressure of 1–3 kgf/cm² at 150° C. The reaction product was post-treated in the same manner as in Example 1 to obtain a nonionic surfactant I.

Comparative Example 2

In the same manner as Comparative Example 1, except using 440 parts (10 moles) of EO instead of 308 parts of EO, a nonionic surfactant II was obtained.

Comparative Example 3

In the same manner as Comparative Example 1, except that 88 parts (2 moles) of EO, 116 parts (2 moles) of PO and 264 parts (6 moles) of EO were successively introduced instead of 308 parts of EO, a nonionic surfactant III was obtained through filtration.

Comparative Example 4

In the same manner as Comparative Example 3, except using 88 parts (2 moles) of EO, 116 parts (2 moles) of PO and 528 parts (12 moles) of EO instead of 88 parts (2 moles) of EO, 116 parts (2 moles) of PO and 264 parts (6 moles) of EO, a nonionic surfactant IV was obtained through filtration.

Comparative Example 5

Into the same vessel as in Example 1, 186 parts (1 mole) of lauryl alcohol was charged; and, after replacing the atmosphere within the vessel with nitrogen, dehydration was carried out for 1 hour at 120° C. under reduced pressure (about 20 mmHg), followed by adding 0.3 part of boron trifluoride diethylether and then replacing the atmosphere within the vessel with nitrogen. Subsequently, 440 parts (10 moles) of EO was introduced under a gauge pressure of 1 kgf/cm² at 50° C. The reaction product was neutralized with an alkali to obtain a nonionic surfactant V. In this Comparative Example, formation of about 6% of byproduct polyetheleneglycol was observed.

Comparative Example 6

In the same manner as Comparative Example 5, except using 88 parts (2 moles) of EO, 116 parts (2 moles) of PO and 264parts (6 moles) of EO instead of 440 parts of EO, a nonionic surfactant VI was obtained through filtration.

TABLE 1

| Ex. No. | Nonionic Surfactant | Mw/Mn Measured value | Mw/Mn Calculated upper limit | Unreacted Alcohol Amount (%) | Distribution constant |
|---|---|---|---|---|---|
| Ex. 1 | B-1 | 1.045 | 1.049 | 0.02 | 0.92 |
| Ex. 2 | B-2 | 1.052 | 1.056 | undetected | — |
| Ex. 3 | B-3 | 1.041 | 1.044 | undetected | — |
| Ex. 4 | B-4 | 1.019 | 1.020 | undetected | — |
| Ex. 5 | A-1 | 1.067 | 1.072 | 0.006 | 0.91 |
| Ex. 6 | A-2 | 1.065 | 1.067 | undetected | — |
| Ex. 7 | A-3 | 1.061 | 1.064 | undetected | — |
| Ex. 8 | A-4 | 1.071 | 1.079 | undetected | — |
| Ex. 9 | A-5 | 1.071 | 1.074 | undetected | — |
| Compar. Ex. 1 | I | 1.089 | 1.049 | 2.9 | 3.70 |
| Compar. Ex. 2 | II | 1.101 | 1.056 | 0.7 | 3.26 |
| Compar. Ex. 3 | III | 1.118 | 1.079 | 0.3 | 2.50 |
| Compar. Ex. 4 | IV | 1.122 | 1.067 | 0.03 | 2.71 |
| Compar. Ex. 5 | V | 1.082 | 1.056 | 0.04 | 1.60 |
| Compar. Ex. 6 | VI | 1.096 | 1.079 | 0.04 | 1.60 |

Example 10

In the same manner as in Example 1, except using 0.01 part instead of 0.02 parts of magnesium sulfate, an EO adduct of lauryl alcohol was obtained. Distribution constant c' of the resulting adduct was 0.42 and the amount of unreacted alcohol being 2.2% (0.032 mole). To this adduct, 0.3 parts of potassium hydroxide was added, and 61.6 parts (1.4 moles) of EO was introduced under a gauge pressure of 1–3 kgf /cm². The reaction product was post-treated in the same manner as in Example 1 to obtain an emulsifier (I-1) comprising a nonionic surfactant of this invention. HLB was 8.9.

Example 11

In the same manner as Example 10, except that 242 parts (1 mole) of cetyl alcohol was used instead of lauryl alcohol and 105.6 parts (2.4 moles) of EO was used instead of 61.6 parts of EO introduced in the presence of the alkaline catalyst to obtain an emulsifier (I-2) comprising a nonionic surfactant of this invention. HLB was 8.9.

Example 12

In the same manner as Example 10, except that 270 parts (1 mole) of stearyl alcohol was used instead of lauryl alcohol and 127.6 parts (2.9 moles) of EO was used instead of 61.6 parts of EO introduced in the presence of the alkaline catalyst to obtain an emulsifier (I-3) comprising a nonionic surfactant of this invention. HLB was 8.9.

Comparative Example 7

Into the same vessel as in Example 1, 186 parts (1 mole) of lauryl alcohol and 0.3 part of potassium hydroxide were charged; and, after replacing the atmosphere within the vessel with nitrogen, dehydration was carried out for 1 hour at 130° C. under reduced pressure (1–5 mmHg). Then, 149.6 parts (3.4 moles) of EO was introduced under a gauge pressure of 1–3 kgf/cm² at 150° C. The reaction product was post-treated in the same manner as in Example 1 to obtain an emulsifier I. HLB was 8.9.

Comparative Example 8

In the same manner as Comparative Example 5, except using 149.6 parts (3.4 moles) of EO instead of 440 parts of EO to obtain an emulsifier II. HLB was 8.9. In this Comparative Example. The formation of about 4% of byproduct polyetheleneglycol was observed.

Comparative Example 9

Into the same vessel as in Example 1, 186 parts (1 mole) of lauryl alcohol and 3.6 part of magnesium perchlorate were charged; and, after replacing the atmosphere within the vessel with nitrogen, dehydration was carried out for 1 hour at 120° C. under reduced pressure (about 20 mmHg). Then, 149.6 parts (3.4 moles) of EO was introduced under a gauge pressure of 1–3 kgf/cm² at 150° C. The reaction product was post-treated in the same manner as in Example 1 to obtain an emulsifier III. HLB was 8.9. In this case, aldehyde odor was severe, and about 3% of high molecular weight materials (dimers such as aldol condensates) were contained as byproducts. Emulsifier III obtained in this Comparative Example was severely colored and of black-brown shades. Average addition molar number of EO determined from hydroxyl number was 2.5 moles.

TABLE 2

| Ex. No. | Nonionic Surfactant | Mw/Mn Measured value | Mw/Mn Calculated upper limit | Unreacted Alcohol Amount (%) | Distribution constant |
|---|---|---|---|---|---|
| Ex. 10 | I-2 | 1.031 | 1.035 | 0.3 | 0.57 |
| Ex. 11 | 1-2 | 1.037 | 1.040 | 0.08 | 0.61 |
| Ex. 12 | 1-3 | 1.038 | 1.042 | 0.05 | 0.65 |
| Ex. 11 | 1-2 | 1.037 | 1.040 | 0.08 | 0.61 |
| Compar. Ex. 7 | I | 1.084 | 1.035 | 10.8 | 3.13 |
| Compar. Ex. 8 | II | 1.063 | 1.035 | 5.5 | 1.77 |
| Compar. Ex.9 | III | 1.058 | 1.028 | 0.5 | 0.39 |

Test Example 1

Using emulsifiers (I-1)–(I-3) obtained in Examples 10–12 and emulsifiers I–III obtained in Comparative Examples 7–9, a mineral oil having an aniline point of 70° C. was emulsified into water to prepare O/W type emulsions. Test conditions are shown below.

Three parts of each emulsifier was blended with 97 parts of the mineral oil, and 5 parts of the blend was thrown into a 100 ml capped measuring cylinder, charged with 95 parts of 10 deionized water separately temperature-conditioned to 25° C.

Then, the measuring cylinder was shaken up and down 20 times and allowed to stand at 25° C. Emulsifed conditions just after, after 30 minutes, 60 minutes and 90 minutes were observed and evaluated by the above-described numerical system of rating. Rating after 60 minutes is emulsifiability index s. The measurement results are shown in Table 3.

TABLE 3

| | Emulsifier | Emulsifiability (Just after emulsification) | Height Emulsion stability After 30 min. | Height Emulsion stability After 60 min. | Height Emulsion stability After 90 min. | (mm) from liq. Surface |
|---|---|---|---|---|---|---|
| Ex. | 1 | 10 | 10 | 10 | 10 | 7 |
|  | 2 | 10 | 10 | 10 | 10 | 5 |
|  | 3 | 10 | 10 | 10 | 10 | 7 |
| Compar. Ex | I | 9 | 5 | 4 | 3 | 22 |
|  | II | 9 | 5 | 4 | 3 | 23 |
|  | III | 9 | 5 | 4 | 3 | 19 |

It is apparent from the results of Table 3 that Examples obtained using each surfactant of this invention as the emulsifier have emulsifiability index of 10 and exhibited excellent emulsifiabilty and emulsion stability, as compared with Comparative Examples, and also showed foaming properties of less than a half of Comparative Examples.

Example 13

Into the same vessel as in Example 1, 219 parts (1 mole) of Dobanol 45 (Trade name, produced by Mitsubishi Chemicals Corp.; a mixture of C14/C15=65/35 and linear content of about 75%), 0.05 part of magnesium perchlorate and 0.02 part of barium sulfate were charged; and, after replacing the atmosphere within the vessel with nitrogen, dehydration was carried out for 1 hour at 130° C. under reduced pressure (1–5 mmHg). Then, 88 parts (2 moles) of EO was introduced under a gauge pressure of 1–3 kgf/cm² at 150° C. Weibull constant of the resulting adduct was 0.38, and the amount of unreacted alcohols was 1.7%. To this adduct, 1.3 parts of potassium hydroxide was added, and 87 parts (1.5 moles) of PO and 492.8 parts (11.2 moles) of EO were introduced successively in this order under a gauge pressure of 1–3 kgf/cm² at 130° C. The reaction product was post-treated in the same manner as in Example 1 to obtain an emulsifier (I-4) of this invention. Clouding point of 2% aqueous solution of the emulsifier (I-4) was 87° C.

Example 14

In the same manner as in Example 13, an EO adduct of Dobanol 45 having Weibull constant of 0.38 was obtained. To this adduct, 0.5 part of potassium hydroxide was added, and 528 parts (12 moles) of EO was introduced under a gauge pressure of 1–3 kgf/cm² at 130° C. The reaction product was post-treated in the same manner as in Example 1 to obtain an emulsifier (I-5) of this invention. Clouding point of 2% aqueous solution of the emulsifier (I-5) was 87° C.

Comparative Example 10

Into the same vessel as in Example 1, 219 parts (1 mole) of Dobanol 45 and 0.3 part of potassium hydroxide were charged; and, after replacing the atmosphere within the vessel with nitrogen, dehydration was carried out for 1 hour at 130° C. under reduced pressure (1–5 mmHg). Then, 88 parts (2 moles) of EO, 87 parts (1.5 moles) of PO and 462 parts (10.5 moles) of EO were introduced successively in this order under a gauge pressure of 1–3 kgf/cm² at 150° C. The reaction product was post-treated in the same manner as in Example 1 to obtain an emulsifier IV. Clouding point of 2% aqueous solution of the emulsifier IV was 87° C.

Comparative Example 11

In the same manner as in Example 10, Dobanol 45 was dehydrated. Then, 484 parts (11 moles) of EO was introduced under a gauge pressure of 1–3 kgf/cm² at 150° C. The reaction product was post-treated in the same manner as in Example 1 to obtain an emulsifiers V.

Test Example 2

Using emulsifiers (I-4) and (I-5) obtained in Examples 13–14 and emulsifiers IV and V obtained in Comparative Examples 10 and 11, and further using a nonylphenol EO 11 moles adduct (HLB: 13.8, freezing point: 16° C., emulsifiability index t: 9) as emulsifier VI, an oxidized polyethylene wax was emulsified under pressure at high temperature to compare emulsifiability. Test conditions are shown below.

Into a stainless pressure vessel, charged were 40 parts of an oxidized polyethylene wax [LUWX OA3, produced by BASF (weight-average molecular weight: 9000–10000, acid number: 22–24)], 11 parts of each emulsifier, 0.5 part of potassium hydroxide and 48.5 parts of deionized water together with ten stainless beads, and after being sealed with nitrogen, emulsification was carried out through shaking for 30 minutes under pressure of 2–3 kgf/cm² at 140° C. The measurement results are shown in Table 4.

TABLE 4

| Ex. No. | Emulsifier | Mw/Mn | Unreacted alcohol amount (%) | HLB | Freezing point (° C.) | Emulsifiability Index t |
|---|---|---|---|---|---|---|
| Ex. 13 | I-4 | 1.063 | Undetected | 13.1 | 14 | 9 |
| Ex. 14 | I-5 | 1.047 | Undetected | 14.1 | 29 | 9 |
| Compar. Ex. 10 | IV | 1.120 | 1 | 13.1 | 16 | 2 |
| Compar. Ex. 11 | V | 1.104 | 0.1 | 13.8 | 32 | 4 |

Evaluation was carried out, in accordance with the above mentioned bases, regarding the state of 1% aqueous dilute solution.

It is apparent from the results of Table 4 that emulsifiers (I) comprizing surfactants (A) and (B) of the invention have emulsifiability comparable to the nonylphenol EO adduct, and (I-4) has an improved low-temperature flowability maintaining emulsifiability. On the other hand, conventional nonionic surfactants of non-alkylphenol type do not provide such emulsifiability, though low-temperature flowability could be improved.

Example 15

In the same manner as in Example 13, except using 0.02 part of magnesium sulfate heptahydrate instead of barium sulfate, an EO adduct of Dobanol 45 was obtained. Weibull constant of the resulting adduct was 0.42, and the amount of unreacted alcohols was 2.2% (0.032 mole). To this adduct, 1 parts of potassium hydroxide was added; and 88 parts (2 moles) of EO, 116 parts (2 moles) of PO and 352 parts (8 moles) of EO were introduced successively in this order under a gauge pressure of 1–3 kgf/cm². The reaction product was post-treated in the same manner as in Example 1 to obtain a detergent (L-1) of this invention. HLB was 12.2.

Upon measuring molecular weight distribution and unreacted aliphatic alcohol amount of this detergent (L-1) through GPC and GC, Mw/Mn was 1.068 [calculated value of the upper limit of Mw/Mn satisfying the relation (3): 1.070], and the amount of unreacted aliphatic alcohols was undetected.

Comparative Example 12

In the same manner as in Comparative Example 11, except using 1.5 parts of potassium hydroxide instead of 0.3 part thereof, Dobanol 45 was dehydrated. Then, 176 parts (4 moles) of EO, 116 parts (2 moles) of PO and 352 parts (8 moles) of EO were introduced successively in this order under a gauge pressure of 1–3 kgf/cm² at 150° C. The reaction product was post-treated in the same manner as in Example 1 to obtain a detergent (VII). HLB was 12.2.

Upon measuring molecular weight distribution and unreacted aliphatic alcohol amount of this detergent (VII) through GPC and GC, Mw/Mn was 1.101 [calculated value of the upper limit of Mw/Mn satisfying the relation (3): 1.070], the amount of unreacted aliphatic alcohols was 0.048% and the calculated value of distribution constant c according to the equation (4) was 2.51.

Test Example 3

Using detergent (L-1) obtained in Example 15, detergent (VII) and a nonylphenol EO 9.5 moles adduct (HLB: 13.1) (VIII), comparative test of detergency was carried out. Test conditions are according to those in the above-mentioned method.

Detergency test is carried out in accordance with Leenerts method (JIS K3370). Six sheets of slide glasses were used as a pair of substrates for soils, and soil components of the above-described composition were used. Using 0.15% concentration aqueous solution of the above detergent liquor as wash liquid, the slide glass coated with the artificial soils was washed; and a detergency is determined according to the above equation, and a detergency index is represented as an index making detergency of nonylphenol EO 9.5 moles adduct (VIII) as 100. The measurement results are shown in Table 5.

TABLE 5

|  | Ex. | Compar. Ex. | Standard |
|---|---|---|---|
| Surfactant | L-1 | VII | VIII |
| Detergency index | 103 | 98 | 100 |
| Aqueous solution (° C.) Cloud point of 2% | 57 | 56 | 55 |

It is apparent from the results of Table 5 that Example obtained using the nonionic surfactant of this invention as the detergent has improved detergency, ac compared with Comparative Example.

Example 16

In the same manner as in Example 15, an EO adduct of Dobanol 45 of the first step was obtained. To this adduct, 0.3 part of potassium hydroxide was added, and 264 parts (6 moles) of EO was introduced under a gauge pressure of 1–3 kgf/cm² at 150° C. The reaction product was post-treated in the same manner as in Example 1 to obtain a-surfactant (H-1)of this invention. HLB was 12.3.

Upon measuring molecular weight distribution and unreacted aliphatic alcohol amount of (H-1) through GPC and GC, Mw/Mn was 1.046 [calculated value of the upper limit of Mw/Mn satisfying the relation (2): 1.052], the amount of unreacted alcohols was 0.003% and the calculated value of distribution constant c according to the equation (4) was 0.83.

Comparative Example 13

Into the same vessel as in Example 1, 219 parts (1 mole) of Dobanol 45 and 1.0 part of potassium hydroxide were charged; and, after replacing the atmosphere within the vessel with nitrogen, dehydration was carried out for 1 hour at 130° C. under reduced pressure (1–5 mmHg). Then, 352 parts (8 moles) of EO was introduced under a gauge pressure of 1–3 kgf/cm² at 150° C. The reaction product was post-treated in the same manner as in Example 1 to obtain a surfactant (IX). HLB was 12.3.

Upon measuring molecular weight distribution and unreacted aliphatic alcohol amount of the surfactant (IX) through GPC and GC, Mw/Mn was 1.092 (calculated value of the upper limit of Mw/Mn satisfying the relation (2): 052], the amount of unreacted alcohols was 1.4% and the calculated value of distribution constant c according to the equation (4) was 3.13.

Test Example 4

Using surfactant (H-1) obtained in Example 16, surfactant (IX) obtained in Comparative Example 13 and a nonylphenol EO 8.5 moles adduct (HLB: 12.6) (X), viscosity of aqueous solution was measured, and a viscosity index is represented as an index making viscosity of nonylphenol EO 8.5 moles adduct (X) as 100. Viscosity measurement was carried out with a Brookfield type viscometer, using a rotor No.3, at 40 rpm, at 25° C. The results are shown in Table 6.

TABLE 6

|  | Ex. | Compar. Ex. | Standard |
|---|---|---|---|
| Surfactant | H-1 | IX | X |
| Concentration of surfactant (%) | 5 | 5 | 5 |
| viscosity (mPa·s) | 360 | 25 | 128 |
| Viscosity index | 280 | 20 | 100 |

It is apparent from the results of Table 6 that the surfactant of this invention shows higher viscosity at the same concentration as Comparative Example and has improved thickening function.

In the following Examples, anionic surfactants are described. Evaluation tests of analysis (molecular weight, contents of unreacted aliphatic alcohols and anionized products) and performances below were carried out according to the following methods.

<<Measurement conditions-2 of GPC>>

Colmun: TSK gel G2500PWXL
Colmun temperature: 40° C.; Detector: RI;
Solvent: water/methanol = 70/30 (0.5% sodium acetate);
Flow rate: 1.0 ml/min.;
Sample concentration: 0.25% by weight; Pour: 200 µl;
Standard: polyoxyethylene glycol (TSK STANDARD POLYETHYLENE OXIDE, produced by Tosoh Corp.)
Data processor: SC-8020 (produced by Tosoh Corp.); or
<<Measurement conditions-3 of GPC>>

Colmun: TSK gels SuperH4000, 3000 and 2000 (all produced by Tosoh Corp.)
Colmun temperature: 40° C.; Detector: RI;
Solvent: tetrahydrofuran;
Flow rate: 0.6 ml/min.;
Sample concentation: 0.25% by weight; Pour: 10 µl;
Standard: polyoxyethylene glycol (TSK STANDARD POLYETHYLENE OXIDE, produced by Tosoh Corp.)
Data processor: SC-8020 (produced by Tosoh Corp.);

-continued

<<Measurement conditions-2 of GC>>

Colmun: Silicone GE-SE30
Detector: FID; Injection: 280° C.;
Heat-up rate: 100–250° C./10° C. min.;
Internal standard; octanol;
<<Measurement conditions-1 of HPLC>>

Colmun: Shimapack CLC-ODS
Elute: methanol/water = 80/20; Flow rate: 1 ml/min.;
Pour: 30 µl; Detector: RI, UV
<Testing method of odor>

Into a 300 ml glass vessel, 50 g of a sample was charged, and odor was judged after allowing it to stand for 1 hour at 300° C.
<Testing method of pH>

Using a pH meter M-12 (produced by Horib-seisakusho Corp.), stock solution was taken to meassurement at 25° C.
<Testingmethod of aqueous solution viscosity>

Viscosity of an aqueous solution was with a BL type viscometer, after temperature-conditioning for 2 hours at 25° C.
<Testing method of stability with time (appearance)>

A detergent composition was charged into a 100 ml glass bottle; and appearance was observed with eyes after allowing it to stand for 30 days within thermostatic chambers of 0° C., 25° C. and 50° C. The sample was grossly observed for appearance and lather height just after was read to give forming properties. in accordance with the following criteria.
Criteria ◯: transparent liquid;
Δ: forming some turbidity (misting)/some tendency of separation;
X: forming remarkable turbidity (misting)/being separated or solidified
<Testing method of stability with time (hue)>

A detergent composition was charged into a 100 mil glass bottle; degree of color development was observed with eyes after allowing it to stand for 30 days within thermostatic chambers of 0° C., 25° C. and 50° C. The sample was grossly observed for coloration in accordance with the following criteria.
Criteria ◯: no color development transparent liquid;
Δ: some color development
X: severe color development
<Testing method of stability with time (odor)>

An anionic surfactant was charged into a 100 ml glass bottle; and degrees of odor development was observed with eyes after allowing it to stand for 30 days within thermostatic chambers of 0° C., 25° C. and 50° C. The organoleptic evaluation was performed for the degree of odor for appearance in accordance with the following criteria.
Criteria ◯: no change;
Δ: some odor;
X: severe odor
<Testing method of forming properties>

With a juicer-mixer (MX-390-GM) of Toshiba, 200 ml of a 0.3% by weight active ingredient concentration aqueous solution of an anionic surfactant was stirred for 30 seconds, and lather height was read to give forming properties. The higher the numerical value, the better are forming properties. Water used was a hard water of 15 ppm (calculated as CaO), and the test was carried out at 30° C.
<Testing method of skin irritation>

A 1.0% (active ingredient) aqueous solution of composition shown in TABLE 3 was prepared; and human patch test (closed, 48 hours, inside of the upper arm) was carried out by panelers (each 5 males and females), who gave marks individually under the following criteria, and evaluation was represented by the total of marks.

-continued

0: no reaction (no red spots);
1: red spots of slight degree;
2: clear red spots;
3: severe red spots
<Testing method of usability>

Usability was tested by make panelers (each 10 males and females), who shampooed their hair with an anionic surfactant, and evaluated with respect to "foaming", "foam quality" and "feeling" in accordance with the following criteria.
Criteria "foaming" "feeling"
○: good;
Δ: ordinary
X: inferior
"foam quality"
○: creamy;
Δ: ordinary;
X: coarse

Example 17

Into a glass vessel, transferred was the first step EO adduct of lauryl alcohol (Weibull distribution constant c': 0.42) prepared in Example 1, and 120 parts (1.03 mole) of chlorosulfonic acid was gradually added dropwise thereto, while maintaining the temperature at 20° C. After carrying out dehydrochlorination for 2 hours at the temperature, the sulfated product was neutralized with an aqueous solution of 41.2 parts (1.03 mole) of sodium hydroxide dissolved in 1110 parts of water to obtain an anionic surfactant containing 25% active ingredients.

Upon measuring molecular weight distribution of the anionic surfactant and unreacted lauryl alcohol sulfate amount through Measurement conditions-2 of GPC and Measurement conditions-1 of HPLC, Mw/Mn was 1.020 [calculated value of the upper limit of Mw/Mn satisfying the relation (3'): 1.031] and the amount of unreacted lauryl alcohol sulfate was 2.3% by weight (0.030 mole) (distribution constant c'=0.41).

Example 18

Into a glass vessel, the nonionic surfactant (B-2) obtained in Example 2 was transferred, and 80 parts (1.0 mole) of sulfan was gradually added dropwise thereto, while maintaining the temperature at 20° C. After continuing stirring for 2 hours at the temperature, the sulfated product was neutralized with an aqueous solution of 40.0 parts (1.0 mole) of sodium hydroxide dissolved in 1374 parts of water to obtain an anionic surfactant containing 25% active ingredients.

Upon measuring molecular weight distribution of the anionic surfactant and unreacted lauryl alcohol sulfate amount through Measurement conditions-2 of GPC and Measurement conditions-1 of HPLC, Mw/Mn was 1.040 [calculated value of the upper limit of Mw/Mn satisfying the relation (3'): 1.052] and the amount of unreacted lauryl alcohol sulfate was 1.50% by weight (0.0242 mole) (distribution constant c'=1.10).

Comparative Example 14

In the same manner as Comparative Example 1, except using 88 parts (2 moles) of EO instead of 308 parts of EO, a lauryl alcohol EO adduct was obtained.

The Mw/Mn of the reaction product measured through Measurement conditions-2 of GPC was 1.07 [calculated value of the upper limit of Mw/Mn satisfying the relation (3'): 1.0308], and the amount of unreacted lauryl alcohol in the whole reaction product measured through Measurement conditions-2 of GC was 38.0% by weight (0.560 mole) (distribution constant c"=11.15).

Into a glass vessel, the reaction product was transferred, and 120 parts (1.03 mole) of chlorosulfonic acid was gradually added dropwise thereto, while maintaining the temperature at 20° C. After carrying out dehydrochlorination for 2 hours at the temperature, the sulfated product was neutralized with an aqueous solution of 41.2 parts (1.03 mole) of sodium hydroxide dissolved in 1110 parts of water to obtain an anionic surfactant containing 25% active ingredients.

Upon measuring molecular weight distribution of the anionic surfactant and unreacted lauryl alcohol sulfate amount through Measurement conditions-2 of GPC and Measurement conditions-1 of HPLC, Mw/Mn was 1.070 [calculated value of the upper limit of Mw/Mn satisfying the relation (3'): 1.0308] and the amount of unreacted aliphatic alcohol sulfate was 38.0% by weight (0.496 mole) (distribution constant c"=7.59).

Using the anionic surfactants obtained in Examples 17 and 18 and the anionic surfactant obtained in Comparative Example 14, evaluation of performances was carried out. The results are shown in Table 7.

It is apparent from the results that the anionic surfactants (sulfates) of this invention are of lower content of unreacted alcohol sulfate and superior with respect to odor, foamability and skin irritation.

TABLE 7

|  | Ex. 17 | Ex. 18 | Compar. Ex. 14 |
| --- | --- | --- | --- |
| Unreacted alcohol | 2.3 mass % | 1.50 | 38.0 |
| (sulfate content) | (0.030 mole) | (0.0242) | (0.496) |
| Odor | no stink | no stink | stinking |
| Foamability | 155 mm | 150 | 130 |
| Skin irritation | 0 | 0 | 15 |

Example 19

Into a stainless autoclave equipped with stirring and temperature-controlling functions, 186 parts (1 mole) of lauryl alcohol, 0.32 part of magnesium perchlorate and 0.03 part of magnesium hydroxide were charged; and, after replacing the atmosphere within the vessel with nitrogen, dehydration was carried out for 1 hour at 120° C. under reduced pressure (about 20 mmHg) Then, 88 parts (2 moles) of EO was introduced under a gauge pressure of 1–3 kgf/cm$^2$ at 150° C. Time required for addition polymerization of EO was 10 hours. To the resulting product, 1.3 parts of potassium hydroxide was added, and 44 parts (1 mole) of EO was introduced and reacted at 130° C.

The Mw/Mn of the reaction product measured through Measurement conditions-3 of GPC was 1.037 [calculated value of the upper limit of Mw/Mn satisfying the relation (2'): 1.043], and the amount of unreacted lauryl alcohol in the whole reaction product measured through Measurement conditions-1 of GC was 2.35% by weight (0.040 mole) (distribution constant c"=0.910).

Into a glass vessel, charged were 216 parts (0.68 mole) of the reaction product and 48 parts (0.34 mole) of phosphoric anhydride, and the reaction was carried out for 8 hours at 65° C. to obtain an esterified product. Then, 6 parts (0.34 mole) of water was added thereto and the reaction was carried out for 2 hours at 65° C. to obtain a monoesterified product.

Subsequently, 54 parts of sodium hydroxide was dissolved into 675 parts of water, followed by adding thereto 270 parts of the above monoesterified product at 60° C. and adjusting pH to 6.5 to obtain an about 30% aqueous solution of salt of phosphate ester of this invention.

Example 20

In the same manner as in Example 19, was prepared the first step EO adduct of lauryl alcohol (before using potassium hydroxide catalyst).

The Mw/Mn of the reaction product measured through Measurement conditions-3 of GPC was 1.020 [calculated value of the upper limit of Mw/Mn satisfying the relation (2'): 1.031], and the amount of unreacted lauryl alcohol in the whole reaction product measured through Measurement conditions-2 of GC was 3.98% by weight (0.0586 mole) (distribution constant c"=0.558).

Into a glass vessel, charged were 207 parts (0.76 mole) of the reaction product and 54 parts (0.38 mole) of phosphoric anhydride, and the reaction was carried out for 7 hours at 80° C. to obtain an esterified product. Then, 7 parts (0.38 mole) of water was added thereto and the reaction was carried out for 2 hours at 80° C. to obtain a monoesterified product.

Subsequently, 60 parts of sodium hydroxide was dissolved into 673 parts of water, followed by adding thereto 268 parts of the above monoesterified product at 70° C. and adjusting pH to 6.5 to obtain an about 30% aqueous solution of salt of phosphoric ester of this invention.

Example 21

In the same manner as in Example 5, prepared was the first step EO adduct of lauryl alcohol (before using potassium hydroxide catalyst). To the resulting reaction product, 1.3 parts of potassium hydroxide was added, followed by reacting 58 parts (1 mole) of propylene oxide (hereinafter referred to as PO) and then 44 parts (1 mole) of EO at 130° C.

The Mw/Mn of the reaction product measured through Measurement conditions-3 of GPC was 1.036 [calculated value of the upper limit of Mw/Mn satisfying the relation (2'): 1.052], and the amount of unreacted lauryl alcohol in the whole reaction product measured through Measurement conditions-2 of GC was 0.21% by weight.

Into a glass vessel, charged were 226 parts (0.60 mole) of the reaction product and 43 parts (0.30 mole) of phosphoric anhydride, and the reaction was carried out for 7 hours at 90° C. to obtain an esterified product. Then, 5 parts (0.28 mole) of water was added thereto and the reaction was carried out for 2 hours at 80° C. to obtain a monoesterified product.

Subsequently, 48 parts (1.2 mole) of sodium hydroxide was dissolved into 678 parts of water, followed by adding thereto 274 parts of the above monoesterified product at 50° C. and adjusting pH to 6.5 to obtain an about 30% aqueous solution of salt of phosphate ester according to this invention.

Comparative Example 15

Lauryl alcohol was dehydrated in the same manner as in Comparative Example 1. Then, 176 parts (4 moles) of EO was introduced under a gauge pressure of 1–3 kgf/cm$^2$ at 150° C.

The Mw/Mn of the reaction product measured through Measurement conditions-3 of GPC was 1.07 [calculated value of the upper limit of Mw/Mn satisfying the relation (2'): 1.043], and the amount of unreacted lauryl alcohol in the whole reaction product measured through Measurement conditions-2 of GC was 18.0% by weight (0.308 mole) (distribution constant c"=4.75).

Into a glass vessel, charged were 216 parts (0.68 mole) of the reaction product and 48 parts (0.34 mole) of phosphoric anhydride, and the reaction was carried out for 8 hours at 65° C. to obtain an esterified product. Then, 6 parts (0.34 mole) of water was added thereto and the reaction was carried out for 2 hours at 65° C. to obtain a monoesterified product. Subsequently, 54 parts of sodium hydroxide was dissolved into 675 parts of water, followed by adding thereto 270 parts of the above monoesterified product at 60° C. and adjusting pH to 6.5 to obtain an about 30% aqueous solution of salt of phosphate ester of the invention.

Comparative Example 16

A lauryl alcohol EO adduct was prepared in the same manner as in Comparative Example 14.

The Mw/Mn of the reaction product measured through Measurement conditions-3 of GPC was 1.07 [calculated value of the upper limit of Mw/Mn satisfying the relation (2'): 1.0308], and the amount of unreacted lauryl alcohol in the whole reaction product measured through Measurement conditions-2 of GC was 38.0% by weight (0.560 mole) (distribution constant c"=11.15).

Into a glass vessel, charged were 207 parts (0.76 mole) of the reaction product and 54 parts (0.38 mole) of phosphoric anhydride, and the reaction was carried out for 7 hours at 80° C. to obtain an esterified product. Then, 7 parts (0.38 mole) of water was added thereto and the reaction was carried out for 2 hours at 80° C. to obtain a monoesterified product. Subsequently, 60 parts of sodium hydroxide was dissolved into 673 parts of water, followed by adding thereto 268 parts of the above monoesterified product at 70° C. and adjusting pH to 6.5 to obtain an about 30% aqueous solution of salt of phosphate ester of the invention.

Using the anionic surfactants obtained in Examples 19–21 and the anionic surfactants obtained in Comparative Examples 15 and 16, evaluation of performances was carried out. The results are shown in Table 8.

It is apparent from the results that the anionic surfactants of this invention provide aqueous solutions of lower viscosity and good results with respect to foamability, stability with time at high temperature, skin irritation and usability.

TABLE 8

|  | Ex. 19 | Ex. 20 | Ex. 21 | Compar. Ex. 15 | Compar. Ex. 16 |
|---|---|---|---|---|---|
| PH (stock solution) | 6.5 | 6.5 | 6.4 | 6.5 | 6.5 |
| Viscosity (cps) of aqueous solution | 400 | 500 | 200 | 6900 | 7800 |
| Stability with time | | | | | |
| 0° C. | | | | | |
| Appearance | ◯ | ◯ | ◯ | Solidified X | Solidified X |
| Hue | ◯ | ◯ | ◯ | ◯ | ◯ |
| Odor | ◯ | ◯ | ◯ | ◯ | ◯ |
| 25° C. | | | | | |
| Appearance | ◯ | ◯ | ◯ | Solidified X | Solidified X |
| Hue | ◯ | ◯ | ◯ | ◯ | ◯ |
| Odor | ◯ | ◯ | ◯ | ◯ | ◯ |
| 50° C. | | | | | |

TABLE 8-continued

|  | Ex. 19 | Ex. 20 | Ex. 21 | Compar. Ex. 15 | Compar. Ex. 16 |
|---|---|---|---|---|---|
| Appearance | ○ | ○ | ○ | Solidified X | Solidified X |
| Hue | ○ | ○ | ○ | Δ | Δ |
| Odor | ○ | ○ | ○ | Δ | Δ |
| Formability (mm) | 140 | 140 | 140 | 100 | 110 |
| Skin irritation | Point0 | Point0 Usability | Point0 | Point8 | Point9 |
| Foaming | ○ | ○ | ○ | X | X |
| Form quality | ○ | ○ | ○ | X | X |
| Feeling | ○ | ○ | ○ | X | X |

Example 22

To the first step EO adduct of lauryl alcohol (Weibull distribution constant c': 0.42), 1.3 part of potassium hydroxide was added, followed by reacting 44 parts of EO at 130° C.

The Mw/Mn of the reaction product measured through Measurement conditions-3 of GPC was 1.037 [calculated value of the upper limit of Mw/Mn satisfying the relation (2'): 1.043], and the amount of unreacted lauryl alcohol in the whole reaction product measured through Measurement conditions-2 of GC was 2.35% by weight (0.040 mole) (distribution constant c"=0.910).

Into a glass vessel, charged were 176 parts (0.55 mole) of the reaction product and 57 parts (0.58 mole) of maleic anhydride, and the reaction was carried out for 8 hours at 65° C. to obtain a monoesterified product. Then, 77 parts (0.61 mole) of sodium sulfite was dissolved in 690 parts of water, followed by adding thereto 233 parts of the above monoesterified product at 60° C. and reacting them for about 5 hours at the temperature to obtain a sulfonated product. Subsequently, pH was adjusted to 6.5 with citric acid or triethanolamine to obtain an about 30% aqueous solution of a salt of sulfosuccinate.

Example 23

In the same manner as in Example 19, a lauryl alcohol EO adduct was prepared.

The Mw/Mn of the reaction product measured through Measurement conditions-3 of GPC was 1.020 [calculated value of the upper limit of Mw/Mn satisfying the relation (2'): 1.031], and the amount of unreacted lauryl alcohol in the whole reaction product measured through Measurement conditions-2 of GC was 3.98% by weight (0.0586 mole) (distribution constant c"=0.0586).

Into a glass vessel, charged were 165 parts (0.60 mole) of the reaction product and 62 parts (0.63 mole) of maleic anhydride, and the reaction was carried out for 8 hours at 65° C. to obtain a monoesterified product. Then, 84 parts (0.67 mole) of sodium sulfite was dissolved in 689 parts of water, followed by adding thereto 227 parts of the above monoesterified product at 60° C. and reacting them for about 5 hours at the temperature to obtain a sulfonated product. Subsequently, pH was adjusted to 7.0 with citric acid or triethanolamine to obtain an about 30% aqueous solution of a salt of sulfosuccinate of this invention.

Example 24

In the same manner as in Example 21, a lauryl alcohol PO-EO adduct was prepared.

The Mw/Mn of the reaction product measured through Measurement conditions-2 of GPC was 1.036 [calculated value of the upper limit of Mw/Mn satisfying the relation (2'): 052], and the amount of unreacted lauryl alcohol in the whole reaction product measured through Measurement conditions-2 of GC was 0.21% by weight.

Into a glass vessel, charged were 188 parts (0.54 mole) of the reaction product and 52 parts (0.53 mole) of maleic anhydride, and the reaction was carried out for 8 hours at 65° C. to obtain a monoesterified product. Then, 69 parts (0.55 mole) of sodium sulfite was dissolved in 691 parts of water, followed by adding thereto 240 parts of the above monoesterified product at 60° C. and reacting them for about 5 hours at the temperature to obtain a sulfonated product. Subsequently, pH was adjusted to 7.5 with citric acid or triethanolamine to obtain an about 30% aqueous solution of a salt of sulfosuccinate of this invention.

Comparative Example 17

In the same manner as in Comparative Example 16, a lauryl alcohol EO adduct was prepared.

The Mw/Mn of the reaction product measured through Measurement conditions-3 of GPC was 1.10 [calculated value of the upper limit of Mw/Mn satisfying the relation (2'): 052], and the amount of unreacted lauryl alcohol in the whole reaction product measured through Measurement conditions-2 of GC was 11.0% by weight (0.214 mole) (distribution constant c"=2.26).

Into a glass vessel, charged were 185 parts (0.51 mole) of the reaction product and 53 parts (0.54 mole) of maleic anhydride, and the reaction was carried out for 8 hours at 65° C. to obtain a monoesterified product. Then, 71 parts (0.56 mole) of sodium sulfite was dissolved in 691 parts of water, followed by adding thereto 238 parts of the above monoesterified product at 60° C. and reacting them for about 5 hours at the temperature to obtain a sulfonated product. Subsequently, pH was adjusted to 6.5 with citric acid or triethanolamine to obtain an about 30% aqueous solution of a salt of sulfosuccinate of the invention.

Comparative Example 18

In the same manner as in Comparative Example 14, except using 0.6 parts of potassium hydroxide instead of 0.3 part thereof, lauryl alcohol was dehydrated. Then, 88 parts (2 moles) of EO, 58 parts (1 mole) of PO and 44 parts (1 mole) of EO were introduced successively in this order under a gauge pressure of 1–3 kgf/cm² at 130° C.

Mw/Mn of the reaction product measured through Measurement conditions-3 of GPC was 1.12 [calculated value of the upper limit of Mw/Mn satisfying the relation (2'): 1.079], and the amount of unreacted lauryl alcohol in the whole reaction product measured through Measurement conditions-2 of GC was 7.3% by weight. (distribution constant c'=2.97).

Into a glass vessel, charged were 188 parts (0.50 mole) of the reaction product and 52 parts (0.53 mole) of maleic anhydride, and the reaction was carried out for 8 hours at 65° C. to obtain a monoesterified product. Then, 69 parts (0.55 mole) of sodium sulfite was dissolved in 691 parts of water, followed by adding thereto 240 parts of the above monoesterified product at 60° C. and reacting them for about 5 hours at the temperature to obtain a sulfonated product.

Subsequently, pH was adjusted to 6.5 with citric acid or triethanolamine to obtain an about 30% aqueous solution of a salt of sulfosuccinate of the invention.

Using the anionic surfactants obtained in Examples 22–24 and the anionic surfactants obtained in Comparative Examples 17 and 18, evaluation of performances was carried out. The results are shown in Table 9.

It is apparent from the results that the anionic surfactants of this invention provide aqueous solutions of lower viscosity and good results with respect to odor, stability with time, foamability, skin irritation and usability.

TABLE 9

|  | Ex. 22 | Ex. 23 | Ex. 24 | Compar. Ex. 17 | Compar. Ex. 18 |
|---|---|---|---|---|---|
| PH (stock solution) | 6.5 | 7.0 | 7.5 | 6.5 | 6.5 |
| Viscosity (cps) of aqueous solution | 50 | 100 | 50 | 6500 | 1000 |
| Stability with time | | | | | |
| 0° C. | | | | | |
| Appearance | ○ | ○ | ○ | Solidified X | Paste X |
| Hue | ○ | ○ | ○ | ○ | ○ |
| Odor | ○ | ○ | ○ | ○ | ○ |
| 25° C. | | | | | |
| Appearance | ○ | ○ | ○ | Solidified X | Solidified X |
| Hue | ○ | ○ | ○ | ○ | ○ |
| Odor | ○ | ○ | ○ | ○ | ○ |
| 50° C. | | | | | |
| Appearance | ○ | ○ | ○ | Solidified X | Solidified X |
| Hue | ○ | ○ | ○ | Δ | ○ |
| Odor | | ○ | ○ | Δ | ○ |
| Formability (mm) | 145 | 145 | 145 | 100 | 105 |
| Skin irritation | Point 0 | Point 0 | Point 0 | Point 8 | Point 5 |
| Usability | | | | | |
| Foaming | ○ | ○ | ○ | X | X |
| Form quality | ○ | ○ | ○ | X | X |
| Feeling | ○ | ○ | ○ | X | X |

Example 25

In the same manner as in Example 19, a lauryl alcohol EO adduct was prepared. To the reaction product, 1.3 part of potassium hydroxide was added, followed by reacting 44 parts of EO at 130° C.

Mw/Mn of the reaction product measured through Measurement conditions-3 of GPC was 1.037 [calculated value of the upper limit of Mw/Mn satisfying the relation (2'): 1.043], and the amount of unreacted lauryl alcohol in the whole reaction product measured through Measurement conditions-2 of GC was 2.35% by weight (0.040 mole) (distribution constant c"=0.910).

Into a glass vessel, charged were 240 parts (0.75 mole) of the reaction product, 97 parts (0.83 mole) of sodium monochloroacetate and 293 parts of toluene, followed by gradually reducing the pressure to degree of vacuum of 75 mmHg while maintaining the temperature at 50° C. Thereafter, 38 parts (0.94 mole) of granulated sodium hydroxide was charged thereto over 2 hours, while carrying dehydration under reduced pressure. Further, aging was carried out for 6 hours. Rate of reaction (degree of etherification) as measured with the above-described liquid chromatography was 96%.

After adding 300 parts of water and acidifying the product with hydrochloric acid, separation of liquid phases, desalting and removal of toluene were carried out. Subsequently, 30 parts (0.75 mole) of sodium hydroxide was dissolved in 700 parts of water, followed by adding thereto the above carboxyetherified product at 60° C. and adjusting pH to 6.5 to obtain an about 30% aqueous solution of a carboxyetherified product of this invention.

Example 26

In the same manner as in Example 19, a lauryl alcohol EO adduct was prepared.

The Mw/Mn of the reaction product measured through Measurement conditions-3 of GPC was 1.020 [calculated value of the upper limit of Mw/Mn satisfying the relation (2'): 1.031], and the amount of unreacted lauryl alcohol in the whole reaction product measured through Measurement conditions-2 of GC was 3.98% by weight (0.0586 mole) (distribution constant c"=0.558).

Into a glass vessel, charged were 232 parts (0.85 mole) of the reaction product, 109 parts (0.93 mole) of sodium monochloroacetate and 284 parts of toluene, followed by gradually reducing the pressure to degree of vacuum of 80 mmHg while maintaining the temperature at 50° C. Thereafter, 42 parts (1.06 mole) of granulated sodium hydroxide was charged thereto over 2 hours, while carrying dehydration under reduced pressure. Further, aging was carried out for 6 hours. Rate of reaction (degree of etherification) as measured with the above-described liquid chromatography was 97%. After adding 300 parts of water and acidifying the product with hydrochloric acid, separation of liquid phases, desalting and removal of toluene were carried out. Subsequently, 35 parts (0.85 mole) of sodium hydroxide was dissolved in 700 parts of water, followed by adding thereto the above carboxyetherified product at 60° C. and adjusting pH to 6.5 to obtain an about 30% aqueous solution of a carboxyetherified product according to this invention.

Example 27

In the same manner as in Example 24, a lauryl alcohol PO-EO adduct was prepared.

Into a glass vessel, charged were 247 parts (0.66 mole) of this reaction product, 84 parts (0.72 mole) of sodium monochloroacetate and 302 parts of toluene, followed by gradually reducing the pressure to degree of vacuum of 75 mmHg while maintaining the temperature at 45° C. Thereafter, while carrying dehydration under reduced pressure, 33 parts (0.82 mole) of granulated sodium hydroxide was charged thereto over 2 hours, followed by carrying out aging for 6 hours. Rate of reaction (degree of etherification) as measured with the above-described liquid chromatography was 96%.

After adding 300 parts of water and acidifying the product with hydrochloric acid, separation of liquid phases, desalting and removal of toluene were carried out. Subsequently, 26 parts (0.66 mole) of sodium hydroxide was dissolved in 700 parts of water, followed by adding thereto the above carboxyetherified product at 60° C. and adjusting pH to 6.5 to obtain an about 30% aqueous solution of a carboxyetherified product of this invention.

Comparative Example 19

In the same manner as in Comparative Example 15, a lauryl alcohol EO adduct was prepared.

The Mw/Mn of the reaction product measured through Measurement conditions-3 of GPC was 1.07 [calculated value of the upper limit of Mw/Mn satisfying the relation (2'): 1.043], and the amount of unreacted lauryl alcohol in the whole reaction product measured through Measurement conditions-2 of GC was 18.0% by weight (0.308 mole) (distribution constant c"=4.75).

Into a glass vessel, charged were 240 parts (0.75 mole) of the reaction product, 97 parts (0.83 mole) of sodium monochloroacetate and 293 parts of toluene, followed by gradually reducing the pressure to degree of vacuum of 75 mmHg while maintaining the temperature at 50° C. Thereafter, 38 parts (0.94 mole) of granulated sodium hydroxide was charged thereto over 2 hours, while carrying dehydration under reduced pressure. Further, aging was carried out for 6 hours. Rate of reaction (degree of etherification) as measured with the above-described liquid chromatography was 96%.

After adding 300 parts of water and acidifying the product with hydrochloric acid, separation of liquid phases, desalting and removal of toluene were carried out. Subsequently, 30 parts (0.75 mole) of sodium hydroxide was dissolved in 700 parts of water, followed by adding thereto the above carboxyetherified product at 60° C. and adjusting pH to 6.5 to obtain an about 30% aqueous solution of a carboxyetherified product according to the invention.

Comparative Example 20

In the same manner as in Comparative Example 14, a lauryl alcohol EO adduct was prepared.

The Mw/Mn of the reaction product measured through Measurement conditions-3 of GPC was 1.07 [calculated value of the upper limit of Mw/Mn satisfying the relation (2'): 1.0308], and the amount of unreacted lauryl alcohol in the whole reaction product measured through Measurement conditions-1 of GC was 38.0% by weight (0.560 mole) (distribution constant c"=11.15) Into a glass vessel, charged were 232 parts (0.85 mole) of the reaction product, 109 parts (0.93 mole) of sodium monochloroacetate and 284 parts of toluene, followed by gradually reducing the pressure to degree of vacuum of 80 mmHg while maintaining the temperature at 50° C. Thereafter, while carrying dehydration under reduced pressure, 42 parts (1.06 mole) of granulated sodium hydroxide was charged thereto over 2 hours, followed by carrying out aging for 6 hours. Rate of reaction (degree of etherification) as measured with the above-described liquid chromatography was 97%.

After adding 300 parts of water and acidifying the product with hydrochloric acid, separation of liquid phases, desalting and removal of toluene were carried out. Subsequently, 35 parts (0.85 mole) of sodium hydroxide was dissolved in 700 parts of water, followed by adding thereto the above carboxyetherified product at 60° C. and adjusting pH to 6.5 to obtain an about 30% aqueous solution of a carboxyetherified product according to the invention.

Using the anionic surfactants obtained in Examples 25–27 and the anionic surfactants obtained in Comparative Examples 19 and 20, evaluation of performances was carried out. The results are shown in Table 10.

It is apparent from the results that the anionic surfactants of this invention provide aqueous solutions of lower viscosity and good results with respect to odor, stability with time, foamability, skin irritation and usability.

TABLE 10

| | Ex. 25 | Ex. 26 | Ex. 27 | Compar. Ex. 19 | Compar. Ex. 20 |
|---|---|---|---|---|---|
| PH (stock solution) | 6.8 | 6.7 | 6.4 | 6.5 | 6.5 |
| Viscosity (cps) of aqueous solution | 400 | 500 | 200 | 5500 | 6800 |
| Stability with time | | | | | |
| 0° C. | | | | | |
| Appearance | ○ | ○ | ○ | Solidified X | Solidified X |
| Hue | ○ | ○ | ○ | ○ | ○ |
| Odor | ○ | ○ | ○ | ○ | ○ |
| 25° C. | | | | | |
| Appearance | ○ | ○ | ○ | Solidified X | Solidified X |
| Hue | ○ | ○ | ○ | ○ | ○ |
| Odor | ○ | ○ | ○ | ○ | ○ |
| 50° C. | | | | | |
| Appearance | ○ | ○ | ○ | Solidified X | Solidified X |
| Hue | ○ | ○ | ○ | Δ | Δ |
| Odor | | ○ | ○ | Δ | Δ |
| Formability (mm) | 142 | 142 | 140 | 112 | 112 |
| Skin irritation | Point 0 | Point 0 | Point 0 | Point 6 | Point 5 |
| Usability | | | | | |
| Foaming | ○ | ○ | ○ | X | X |
| Form quality | ○ | ○ | ○ | X | X |
| Feeling | ○ | ○ | ○ | X | X |

Detergent compositions of Examples 28–36 and Comparative Examples 21–23 were prepared according to the formulation as shown in Tables 11 and 12. Evaluation of performances of the detergent composition was shown in Table 13. Evaluation tests of performances are in accordance with the foregoing methods. Detergency index of anionic surfactants is in accordance with the following method.

Measuring Method of Detergency Index of Anionic Surfactant

Hereinafter, % means % by weight.

| <<Formulation of Detergent Liquor>> | |
|---|---|
| Anionic surfactant | 10% |
| Coconut oil fatty acid amidopropyl-dimethyl betain | 5% |
| 1:1 Mole type coconut oil fatty acid diethanolamide | 1% |
| Water | 84% |
| Total | 100% |

Detergency test was carried out in accordance with Leenerts method (JIS K3370), using a detergent liquor formulated according to the above formulation. Six sheets of slide glasses were used as a pair of substrates for soils, and a chloroform solution of artificial soils of the following composition as soil components is used for coating. The slide glass coated with the artificial soils is washed with an aqueous solution of 0.3% concentration, as a wash liquid, of the detergent liquor; and a detergency is determined according to the following equation, and a detergency index is represented as an index making detergency of lauryl alcohol EO 2 moles adduct obtained in Comparative Example 14 as 100.

| <Composition of Artificial Dirt Components>> | |
|---|---|
| Myristic acid | 15% |
| Oleic acid | 15% |
| Tristearin | 15% |
| Triolein | 15% |
| Cholesterol stearate | 2% |
| Paraffin wax | 10% |
| Squalene | 10% |
| Cholesterol | 8% |
| Bovine serum albumin | 10% |
| Total | 100% |

Detergency (%) = 100 × (Amount of soils (g) before washing − Amount of soils (g) after washing)/− Amount of soils (g) before washing

TABLE 11

| | Example | | | | | | |
|---|---|---|---|---|---|---|---|
| | 28 | 29 | 30 | 31 | 32 | 33 | 34 |
| Ex. 17 sulfate | 20 | 13 | | | | | |
| Ex. 18 sulfate | | | 13 | | | | |
| Ex. 19 phosphate | | | | 13 | | | |
| Ex. 20 phosphate | | | | | 13 | | |
| Ex. 22 sulfosuccinate | | | | | | 13 | |
| Ex. 23 sulfosuccinate | | | | | | | 13 |
| Coconut oil fatty acid diethanolamide | 2 | 0 | 2 | 7 | 2 | 2 | |
| Lauryl dimethyl betain | 5 | 7 | 5 | 0 | 5 | 5 | |
| Water | 80 | 80 | 80 | 80 | 80 | 80 | 80 |
| Total | 100 | 100 | 100 | 100 | 100 | 100 | 100 |

Numberical value represents active ingredient (% by weight).

TABLE 12

| | Ex. | | Compar. Ex. | | | Standard |
|---|---|---|---|---|---|---|
| | 35 | 36 | 21 | 22 | 23 | |
| Ex. 25 carboxylether | 13 | | | | | |
| Ex. 26 carboxylether | | 13 | | | | |
| Compar. Ex. 14 sulfate | | | | | | 13 |
| Compar. Ex. 15 phosphate | | | 13 | | | |
| Compar. Ex. 16 phosphate | | | | 13 | | |
| Compar. Ex. 17 sulfosuccinate | | | | | 13 | |
| Compar. Ex. 19 carboxylether | | | | | | |
| Coconut oil fatty acid diethanolamide | 2 | 2 | 2 | 2 | 2 | 2 |
| Lauryl dimethyl betain | 5 | 5 | 5 | 5 | 5 | |
| Water | 80 | 80 | 80 | 80 | 80 | 80 |
| Total | 100 | 100 | 100 | 100 | 100 | 100 |

TABLE 13

| | Stability with time | | | | Usability | | | Detergency |
|---|---|---|---|---|---|---|---|---|
| Ex. No. | Appearance | Odor | Foamability | Skin irritation | Foaming | Foam quality | Feeling | index |
| Ex. 28 | ○ | ○ | 142 | 0 | ○ | ○ | ○ | 122 |
| 29 | ○ | ○ | 145 | 0 | ○ | ○ | ○ | 120 |
| 30 | ○ | ○ | 145 | 0 | ○ | ○ | ○ | 119 |
| 31 | ○ | ○ | 142 | 0 | ○ | ○ | ○ | 115 |
| 32 | ○ | ○ | 142 | 0 | ○ | ○ | ○ | 116 |
| 33 | ○ | ○ | 143 | 0 | ○ | ○ | ○ | 110 |
| 34 | ○ | ○ | 142 | 0 | ○ | ○ | ○ | 112 |
| 35 | ○ | ○ | 145 | 0 | ○ | ○ | ○ | 120 |
| 36 | ○ | ○ | 145 | 0 | ○ | ○ | ○ | 120 |
| Compar. Ex. 21 | X | Δ | 130 | 2 | Δ | Δ | X | 98 |
| 22 | Δ | Δ | 125 | 2 | Δ | X | X | 92 |
| 23 | Δ | X | 129 | 3 | Δ | Δ | X | 95 |
| Standard | X | Δ | 135 | 3 | Δ | Δ | X | 100 |

It is apparent from the results that the detergent compositions of this invention have higher detergency index and odor together with good usability, therefor these are excellent as detergents.

Industrial Applicability

Nonionic surfactants according to the present invention have surface-activities, such as emulsifibility, solubilizing power, detergency and penetrating power. Therefore, they are useful in various surfactant applications, for example, emulsifiers, such as emulsifiers for metal working, emulsifiers for agrochemical emulsions, emulsifiers for cosmetics, emulsifiers for aqueous coatings and emulsifiers for emulsion polymerization; dispersants of agents for paper, such as pigments and salts of fatty acids; solubilizers of perfumes and the like; detergents, as household detergents, such as detergents for clothes and dish-washing detergents, and as industrial detergents, such as detergents for machinery metals; penetrating agents; wetting agents; and defoamers.

Since it has been pointed out that alkylphenol-based nonionic surfactants having been commonly used heretofore in these applications have a fear of environmental hormone (environmental endocrine disrupters ); nonionic surfactants according to this invention, which are non-alkylphenol-based nonionic surfactants of excellent performances, are useful as substitute for them in various applications.

Besides, anionic surfactants of this invention exhibit excellent surface-activities, such as detergency, forming properties and penetrating power. Therefore, they are useful, in addition to the above uses of nonionic surfactants, as shampoos, dish-washing detergents and detergents for hard surfaces such as metals. They are particularly useful as detergents, such as shampoos and detergents for cosmetics, since low temperature stability, odor and irritation are improved through anionization because of lower content of unreacted aliphatic alcohols in aliphatic alcohol alkylene oxide adducts before anionization.

What is claimed is:

1. A nonionic surfactant comprising an aliphatic alcohol alkylene oxide adduct (A),
    said (A) being directly produced by adding an alkylene oxide (b1) to an aliphatic alcohol (a1) and satisfying the following (i), (ii) and (iii):
        (i) comprising one compound represented by the following formula (1) or a mixture of two or more thereof:

$$R^1O-[(C_2H_4O)_m/(AO)_n]-(C_2H_4O)_p-H \quad (1)$$

wherein $R^1$ is an aliphatic hydrocarbon group containing 8–24 carbon atoms or a cycloaliphatic hydrocarbon group containing 8–24 carbon atoms; A is an alkylene group containing at least 3 carbon atoms; m is 0 or an integer of 1 or more, the average thereof being in the range of 0–4, n is 0 or an integer of 1 or more, the average thereof being in the range of 0–3, p is 0 or an integer of 1 or more, the average thereof being in the range of 1–80, (m+n+p) is an integer, the average thereof being in the range of 3–81, and the average of (m+p)/(m+n+p) is at least 0.5; and, in the case of m≠0 and n≠0, $\{(C_2H_4O)m/(AO)n\}$ represents block addition or random addition;
        (ii) having a ratio Mw/Mn of a weight-average molecular weight (Mw) to a number-average molecular weight (Mn) satisfying the following relation (2) or (3):

$$Mw/Mn \leq 0.030 \times Ln(v)+1.010 \text{ (in case of } v<10) \quad (2)$$

$$Mw/Mn \leq -0.026 \times Ln(v)+1.139 \text{ (in case of } v \geq 10) \quad (3)$$

wherein v represents the average of (m+n+p) in the above general formula (1); and
        (iii) having a distribution constant (c), determined byte following equation (4), of 1.0 or less, this being required only in case of v up to 12:

$$c=(v+n_0/n_{00}-1/(Ln(n_{00}/n_0)+n_0/n_{00}-1) \quad (4)$$

wherein v is the same in the above, $n_{00}$ represents the molar number of the aliphatic alcohol (a1) used in the reaction, and $n_0$ represents the molar number of the aliphatic alcohol (a1) unreacted.

2. The nonionic surfactant according to claim 1,
    wherein the n in the general formula (1) is 0 or an integer of 1 or more, the average thereof being in the range of 1–3.

3. The nonionic surfactant according to claim 1,
    wherein then in the general formula (1) is 0, and
    the (A) has a ratio Mw/Mn of a weight-average molecular weight (Mw) to a number-average molecular weight (Mn) satisfying the following relation (6) or (7) instead of the relation (2) or (3):

$$Mw/Mn \leq 0.020 \times Ln(v)+1.010 \text{ (in case of } v<10) \quad (6)$$

$$Mw/Mn \leq -0.026 \times Ln(v)+1.116 \text{ (in case of } v \geq 10) \quad (7)$$

wherein v represents the average of (m+p) in the above general formula (1).

4. The nonionic surfactant according to claim 1,
    which satisfies any of the following (v)–(viii):
        (v) comprising (A) having an HLB of 5–13,
    and having an emulsifiability index s for a mineral oil, having an aniline point of 70° C. and a viscosity of 15–25 mPa·s at 25° C., of at least 8;
        (vi) comprising (A) having an HLD of 11–19,
    and having an emulsifiability index t for an oxidized polyethylene wax, having a weight-average molecular weight of 9000–10000 and an acid number of 22–24, of at least 8;
        (vii) comprising (A) having an HLB of 7–15,
    and having a index of detergency for a synthetic dirts of the following formulation, supported on a slide glass, of at least 100:

| (synthetic dirts formulation) | |
|---|---|
| tallow | 16.6% |
| soybean oil | 16.6% |
| monoolein | 0.4% |
| oil red | 0.2% |
| chloroform | 66.2% |
| total | 100.0%; |

(viii) comprising (A) having an HLB of 10–14, and having a viscosity index of 5% aqueous solution of at least 50.

5. The nonionic surfactant according to claim 1,
    wherein (A) is one having a freezing point satisfying the following relation (9) and having an HLB of 7–15:

$$1.61x-102 \leq y \leq 1.61x-92 \quad (9)$$

wherein x represents % by weight of the units represented by $(C_2H_4O)$ in the general formula (1) formed by addition of ethylene oxide, and y represents the freezing point (° C.) of (A).

6. The nonionic surfactant according to claim 1,
    wherein said (a1) is one selected from the group consisting of saturated aliphatic alcohols, unsaturated aliphatic alcohols and cycloaliphatic alcohols, containing 8–24 carbon atoms.

7. The nonionic surfactant according to claim 1,
    wherein said (a1) is one or two or more selected from the group consisting of octyl alcohol, nonyl alcohol, decyl alcohol, undecyl alcohol, dodecy alcohol, tridecyl alcohol, myristyl alcohol, cetyl alcohol, stearyl alcohol, nonadecyl alcohol, octenyl alcohol, decenyl alcohol, dodecenyl alcohol, tridecenyl alcohol, pentadecenyl alcohol, oleyl alcohol, gadoleyl alcohol, linoleyl alcohol, ethylcyclohexyl alcohol, propylcyclohexyl alcohol, octylcyclohexyl alcohol, nonylcyclohexyl alcohol and adamantyl alcohol.

8. An emulsifier, dispersant, solubilizer, detergent, penetrating agent or wetting agent, comprising the nonionic surfactant according to claim 1.

9. An emulsifier, dispersant, solubilizer, detergent, penetrating agent or wetting agent, comprising the nonionic surfactant according to claim 2.

10. An emulsifier, dispersant, solubilizer, detergent, penetrating agent or wetting agent, comprising the nonionic surfactant according to claim 3.

11. An emulsifier, dispersant, solubilizer, detergent, penetrating agent or wetting agent, comprising the nonionic surfactant according to claim 4.

12. An emulsifier, dispersant, solubilizer, detergent, penetrating agent or wetting agent, comprising the nonionic surfactant according to claim 5.

13. An emulsifier, dispersant, solubilizer, detergent, penetrating agent or wetting agent, comprising the nonionic surfactant according to claim 6.

14. An emulsifier, dispersant, solubilizer, detergent, penetrating agent or wetting agent, comprising the nonionic surfactant according to claim 7.

* * * * *